(12) United States Patent
Schieber et al.

(10) Patent No.: US 12,376,988 B2
(45) Date of Patent: *Aug. 5, 2025

(54) APPARATUS FOR DELIVERING OCULAR IMPLANTS INTO AN ANTERIOR CHAMBER OF THE EYE

(71) Applicant: Alcon Inc., Fribourg (CH)

(72) Inventors: Andrew T. Schieber, St. Louis Park, MN (US); Iqbal K. Ahmed, Mississauga (CA)

(73) Assignee: Alcon Inc., Fribourg (CH)

( * ) Notice: Subject to any disclaimer, the term of this patent is extended or adjusted under 35 U.S.C. 154(b) by 154 days.

This patent is subject to a terminal disclaimer.

(21) Appl. No.: 18/334,256

(22) Filed: Jun. 13, 2023

(65) Prior Publication Data

US 2023/0398021 A1    Dec. 14, 2023

Related U.S. Application Data

(63) Continuation of application No. 16/805,217, filed on Feb. 28, 2020, now Pat. No. 11,712,369, which is a continuation of application No. 14/440,610, filed as application No. PCT/US2013/072001 on Nov. 26, 2013, now Pat. No. 10,617,558.

(60) Provisional application No. 61/730,895, filed on Nov. 28, 2012.

(51) Int. Cl.
*A61F 9/00* (2006.01)
*A61F 9/007* (2006.01)

(52) U.S. Cl.
CPC ........ *A61F 9/0017* (2013.01); *A61F 9/00781* (2013.01)

(58) Field of Classification Search
CPC .................... A61F 9/0017; A61F 9/00781
See application file for complete search history.

(56) References Cited

U.S. PATENT DOCUMENTS

| | | |
|---|---|---|
| 703,296 A | 6/1902 | Nueesch |
| 1,601,709 A | 10/1926 | Anderson |
| 2,716,983 A | 9/1955 | Windischman et al. |
| 3,071,135 A | 1/1963 | Baldwin et al. |

(Continued)

FOREIGN PATENT DOCUMENTS

| | | |
|---|---|---|
| AU | 199876197 | 2/1999 |
| CN | 1950091 | 4/2007 |

(Continued)

OTHER PUBLICATIONS

Bahler, et al., "Trabecular bypass stents decrease intraocular pressure in cultured human anterior segments," *Amer. Journal of Ophthalmology*, vol. 138(6), pp. 988-994, Dec. 2004.

(Continued)

*Primary Examiner* — Richard G Louis
(74) *Attorney, Agent, or Firm* — Levine Bagade Han LLP

(57) ABSTRACT

An ocular implant adapted to be disposed within Schlemm's canal of a human eye with a body extending along a curved longitudinal central axis in a curvature plane, a first strut on one side of the implant and a second strut on an opposite side of the implant, the circumferential extent of the first strut with respect to the plane of curvature being greater than the circumferential extent of the second strut with respect to the plane of curvature. The invention also includes methods of using the implant.

14 Claims, 18 Drawing Sheets

(56) References Cited

U.S. PATENT DOCUMENTS

| | | |
|---|---|---|
| 3,788,327 A | 1/1974 | Donowitz et al. |
| 3,811,442 A | 5/1974 | Maroth |
| 3,858,577 A | 1/1975 | Bass et al. |
| 3,884,236 A | 5/1975 | Krasnov |
| 3,948,271 A | 4/1976 | Akiyama |
| 3,982,541 A | 9/1976 | L'esperance |
| 4,037,604 A | 7/1977 | Newkirk |
| 4,134,405 A | 1/1979 | Smit |
| 4,273,109 A | 6/1981 | Enderby |
| 4,391,275 A | 7/1983 | Fankhauser et al. |
| 4,428,746 A | 1/1984 | Mendez |
| 4,457,757 A | 7/1984 | Molteno |
| 4,461,294 A | 7/1984 | Baron |
| 4,470,407 A | 9/1984 | Hussein |
| 4,497,319 A | 2/1985 | Sekine et al. |
| 4,501,274 A | 2/1985 | Skjaerpe |
| 4,517,973 A | 5/1985 | Sunago et al. |
| 4,538,608 A | 9/1985 | L'esperance |
| 4,548,205 A | 10/1985 | Armeniades et al. |
| 4,551,129 A | 11/1985 | Coleman et al. |
| 4,558,698 A | 12/1985 | O'dell |
| 4,559,942 A | 12/1985 | Eisenberg |
| 4,566,438 A | 1/1986 | Liese et al. |
| 4,580,559 A | 4/1986 | L'esperance |
| 4,583,539 A | 4/1986 | Karlin et al. |
| 4,601,713 A | 7/1986 | Fuqua |
| 4,604,087 A | 8/1986 | Joseph |
| 4,633,866 A | 1/1987 | Peyman et al. |
| 4,658,816 A | 4/1987 | Ector |
| 4,660,546 A | 4/1987 | Herrick et al. |
| 4,671,273 A | 6/1987 | Lindsey |
| 4,689,040 A | 8/1987 | Thompson |
| 4,699,140 A | 10/1987 | Holmes et al. |
| 4,706,669 A | 11/1987 | Schlegel |
| 4,722,350 A | 2/1988 | Armeniades et al. |
| 4,722,724 A | 2/1988 | Schocket |
| 4,729,373 A | 3/1988 | Peyman |
| 4,733,665 A | 3/1988 | Palmaz |
| 4,750,901 A | 6/1988 | Molteno |
| 4,770,654 A | 9/1988 | Rogers et al. |
| 4,791,927 A | 12/1988 | Menger |
| 4,826,478 A | 5/1989 | Schocket |
| 4,846,172 A | 7/1989 | Berlin |
| 4,861,341 A | 8/1989 | Woodburn |
| 4,876,250 A | 10/1989 | Clark |
| 4,880,000 A | 11/1989 | Holmes et al. |
| 4,886,488 A | 12/1989 | White |
| 4,919,130 A | 4/1990 | Stoy et al. |
| 4,925,299 A | 5/1990 | Meisberger et al. |
| 4,934,363 A | 6/1990 | Smith et al. |
| 4,934,809 A | 6/1990 | Volk |
| 4,936,825 A | 6/1990 | Ungerleider |
| 4,946,436 A | 8/1990 | Smith |
| 4,968,296 A | 11/1990 | Ritch et al. |
| 4,994,060 A | 2/1991 | Rink et al. |
| 5,034,010 A | 7/1991 | Kittrell et al. |
| 5,092,837 A | 3/1992 | Ritch et al. |
| 5,123,902 A | 6/1992 | Muller et al. |
| 5,127,901 A | 7/1992 | Odrich |
| 5,129,895 A | 7/1992 | Vassiliadis et al. |
| 5,178,604 A | 1/1993 | Baerveldt et al. |
| 5,180,362 A | 1/1993 | Worst |
| 5,190,552 A | 3/1993 | Kelman |
| 5,213,569 A | 5/1993 | Davis |
| 5,246,452 A | 9/1993 | Sinnott |
| 5,254,112 A | 10/1993 | Sinofsky et al. |
| 5,273,056 A | 12/1993 | Mclaughlin et al. |
| 5,290,267 A | 3/1994 | Zimmermann |
| 5,300,020 A | 4/1994 | L'esperance |
| 5,359,685 A | 10/1994 | Waynant et al. |
| 5,360,399 A | 11/1994 | Stegmann |
| 5,371,078 A | 12/1994 | Clark et al. |
| 5,372,577 A | 12/1994 | Ungerleider |
| 5,445,637 A | 8/1995 | Bretton |
| 5,454,796 A | 10/1995 | Krupin |
| 5,458,615 A | 10/1995 | Klemm et al. |
| 5,501,274 A | 3/1996 | Nguyen et al. |
| 5,536,259 A | 7/1996 | Utterberg |
| 5,575,780 A | 11/1996 | Saito |
| 5,591,223 A | 1/1997 | Lock et al. |
| 5,607,966 A | 3/1997 | Hellberg et al. |
| 5,613,972 A | 3/1997 | Lee et al. |
| 5,626,558 A | 5/1997 | Suson |
| 5,643,250 A | 7/1997 | O'donnell |
| 5,653,753 A | 8/1997 | Brady et al. |
| 5,657,760 A | 8/1997 | Ying et al. |
| 5,676,669 A | 10/1997 | Colvard |
| 5,704,907 A | 1/1998 | Nordquist et al. |
| 5,713,844 A | 2/1998 | Peyman |
| 5,722,970 A | 3/1998 | Colvard et al. |
| 5,738,676 A | 4/1998 | Hammer et al. |
| 5,738,677 A | 4/1998 | Colvard et al. |
| 5,785,658 A | 7/1998 | Benaron et al. |
| 5,792,099 A | 8/1998 | Decamp et al. |
| 5,792,103 A | 8/1998 | Schwartz et al. |
| 5,807,302 A | 9/1998 | Wandel |
| 5,811,453 A | 9/1998 | Yanni et al. |
| 5,865,831 A | 2/1999 | Cozean et al. |
| 5,868,697 A | 2/1999 | Richter et al. |
| 5,879,319 A | 3/1999 | Pynson et al. |
| 5,885,279 A | 3/1999 | Bretton |
| 5,893,837 A | 4/1999 | Eagles et al. |
| 5,895,831 A | 4/1999 | Brasier et al. |
| 5,919,171 A | 7/1999 | Kira et al. |
| 5,948,427 A | 9/1999 | Yamamoto et al. |
| 5,968,058 A | 10/1999 | Richter et al. |
| 5,984,963 A | 11/1999 | Ryan et al. |
| 5,990,099 A | 11/1999 | Clark |
| 5,993,438 A | 11/1999 | Juhasz et al. |
| 5,997,531 A | 12/1999 | Loeb et al. |
| 6,002,480 A | 12/1999 | Izatt et al. |
| 6,007,511 A | 12/1999 | Prywes |
| 6,050,970 A | 4/2000 | Baerveldt |
| 6,083,193 A | 7/2000 | Kadziauskas et al. |
| 6,099,521 A | 8/2000 | Shadduck |
| 6,102,045 A | 8/2000 | Nordquist et al. |
| 6,142,990 A | 11/2000 | Burk |
| 6,146,375 A | 11/2000 | Juhasz et al. |
| 6,177,544 B1 | 1/2001 | Kanai et al. |
| 6,186,974 B1 | 2/2001 | Allan et al. |
| 6,217,584 B1 | 4/2001 | Nun |
| 6,221,078 B1 | 4/2001 | Bylsma |
| 6,238,409 B1 | 5/2001 | Hojeibane |
| 6,241,721 B1 | 6/2001 | Cozean et al. |
| D444,874 S | 7/2001 | Haffner et al. |
| 6,297,228 B1 | 10/2001 | Clark |
| 6,319,274 B1 | 11/2001 | Shadduck |
| 6,328,747 B1 | 12/2001 | Nun |
| 6,375,642 B1 | 4/2002 | Grieshaber et al. |
| 6,398,809 B1 | 6/2002 | Hoffmann et al. |
| 6,409,752 B1 | 6/2002 | Boatman et al. |
| 6,450,984 B1 | 9/2002 | Lynch et al. |
| 6,464,724 B1 | 10/2002 | Lynch et al. |
| 6,471,666 B1 | 10/2002 | Odrich |
| 6,494,857 B1 | 12/2002 | Neuhann |
| 6,508,779 B1 | 1/2003 | Suson |
| 6,517,523 B1 | 2/2003 | Kaneko et al. |
| 6,524,275 B1 | 2/2003 | Lynch et al. |
| 6,533,764 B1 | 3/2003 | Haffner et al. |
| 6,533,768 B1 | 3/2003 | Hill |
| 6,544,208 B2 | 4/2003 | Ethier et al. |
| 6,544,249 B1 | 4/2003 | Yu et al. |
| 6,551,289 B1 | 4/2003 | Higuchi et al. |
| 6,626,858 B2 | 9/2003 | Lynch et al. |
| 6,638,239 B1 | 10/2003 | Bergheim et al. |
| 6,666,841 B2 | 12/2003 | Gharib et al. |
| 6,699,210 B2 | 3/2004 | Williams et al. |
| 6,699,211 B2 | 3/2004 | Savage |
| 6,702,790 B1 | 3/2004 | Ross et al. |
| 6,726,676 B2 | 4/2004 | Stegmann et al. |
| D490,152 S | 5/2004 | Myall et al. |
| 6,730,056 B1 | 5/2004 | Ghaem et al. |
| 6,736,791 B1 | 5/2004 | Tu et al. |
| 6,780,164 B2 | 8/2004 | Bergheim et al. |

(56) References Cited

U.S. PATENT DOCUMENTS

| | | |
|---|---|---|
| 6,783,544 B2 | 8/2004 | Lynch et al. |
| 6,827,699 B2 | 12/2004 | Lynch et al. |
| 6,827,700 B2 | 12/2004 | Lynch et al. |
| 6,881,198 B2 | 4/2005 | Brown |
| 6,899,717 B2 | 5/2005 | Weber et al. |
| 6,939,298 B2 | 9/2005 | Brown et al. |
| 6,955,656 B2 | 10/2005 | Bergheim et al. |
| 6,962,573 B1 | 11/2005 | Wilcox |
| 6,981,958 B1 | 1/2006 | Gharib et al. |
| 6,989,007 B2 | 1/2006 | Shadduck |
| 7,018,376 B2 | 3/2006 | Webb et al. |
| 7,094,225 B2 | 8/2006 | Tu et al. |
| 7,125,119 B2 | 10/2006 | Farberov |
| 7,133,137 B2 | 11/2006 | Shimmick |
| 7,135,009 B2 | 11/2006 | Tu et al. |
| 7,147,650 B2 | 12/2006 | Lee |
| 7,163,543 B2 | 1/2007 | Smedley et al. |
| 7,186,232 B1 | 3/2007 | Smedley et al. |
| 7,192,412 B1 | 3/2007 | Zhou et al. |
| 7,207,965 B2 | 4/2007 | Simon |
| 7,207,980 B2 | 4/2007 | Christian et al. |
| 7,220,238 B2 | 5/2007 | Lynch et al. |
| 7,273,475 B2 | 9/2007 | Tu et al. |
| 7,297,130 B2 | 11/2007 | Bergheim et al. |
| 7,331,984 B2 | 2/2008 | Tu et al. |
| 7,488,303 B1 | 2/2009 | Haffner et al. |
| 7,699,882 B2 | 4/2010 | Stamper et al. |
| 7,740,604 B2 | 6/2010 | Schieber et al. |
| 7,931,596 B2 | 4/2011 | Rachlin et al. |
| 7,967,772 B2 | 6/2011 | Mckenzie et al. |
| 8,012,115 B2 | 9/2011 | Karageozian |
| 8,123,729 B2 | 2/2012 | Yamamoto et al. |
| 8,172,899 B2 | 5/2012 | Silvestrini et al. |
| 8,267,882 B2 | 9/2012 | Euteneuer et al. |
| 8,282,592 B2 | 10/2012 | Schieber et al. |
| 8,308,701 B2 | 11/2012 | Horvath et al. |
| 8,337,509 B2 | 12/2012 | Schieber et al. |
| 8,372,026 B2 | 2/2013 | Schieber et al. |
| 8,414,518 B2 | 4/2013 | Schieber et al. |
| 8,425,449 B2 | 4/2013 | Wardle et al. |
| 8,475,374 B2 | 7/2013 | Irazoqui et al. |
| 8,512,404 B2 | 8/2013 | Frion et al. |
| 8,529,494 B2 | 9/2013 | Euteneuer et al. |
| 8,540,659 B2 | 9/2013 | Berlin |
| 8,551,166 B2 | 10/2013 | Schieber et al. |
| 8,629,161 B2 | 1/2014 | Mizuno et al. |
| 8,636,647 B2 | 1/2014 | Silvestrini et al. |
| 8,647,659 B2 | 2/2014 | Robinson et al. |
| 8,657,776 B2 | 2/2014 | Wardle et al. |
| 8,663,150 B2 | 3/2014 | Wardle et al. |
| 8,663,303 B2 | 3/2014 | Horvath et al. |
| 8,734,377 B2 | 5/2014 | Schieber et al. |
| 8,808,222 B2 | 8/2014 | Schieber et al. |
| 8,939,906 B2 | 1/2015 | Huang et al. |
| 8,939,948 B2 | 1/2015 | De Juan et al. |
| 8,945,038 B2 | 2/2015 | Yablonski |
| 8,951,221 B2 | 2/2015 | Stegmann et al. |
| 8,961,447 B2 | 2/2015 | Schieber et al. |
| 8,974,511 B2 | 3/2015 | Horvath et al. |
| 9,039,650 B2 | 5/2015 | Schieber et al. |
| 9,050,169 B2 | 6/2015 | Schieber et al. |
| 9,066,750 B2 | 6/2015 | Wardle et al. |
| 9,066,783 B2 | 6/2015 | Euteneuer et al. |
| 9,155,655 B2 | 10/2015 | Schieber et al. |
| 9,211,213 B2 | 12/2015 | Wardle et al. |
| 9,226,852 B2 | 1/2016 | Schieber et al. |
| 9,301,875 B2 | 4/2016 | Tu et al. |
| 9,351,874 B2 | 5/2016 | Schieber et al. |
| 9,358,156 B2 | 6/2016 | Wardle et al. |
| 9,402,767 B2 | 8/2016 | Schieber et al. |
| 9,510,973 B2 | 12/2016 | Wardle |
| 9,579,234 B2 | 2/2017 | Wardle et al. |
| 9,603,741 B2 | 3/2017 | Berlin |
| 9,610,196 B2 | 4/2017 | Schieber et al. |
| 9,636,254 B2 | 5/2017 | Yu et al. |
| 9,642,746 B2 | 5/2017 | Berlin |
| 9,693,899 B2 | 7/2017 | Wardle et al. |
| 9,693,901 B2 | 7/2017 | Horvath et al. |
| 9,693,902 B2 | 7/2017 | Euteneuer et al. |
| 9,730,638 B2 | 8/2017 | Haffner et al. |
| 9,757,276 B2 | 9/2017 | Penhasi |
| 9,775,729 B2 | 10/2017 | Mcclain et al. |
| 9,782,293 B2 | 10/2017 | Doci |
| 9,788,999 B2 | 10/2017 | Schaller |
| 9,795,503 B2 | 10/2017 | Perez et al. |
| 9,808,373 B2 | 11/2017 | Horvath et al. |
| 9,820,883 B2 | 11/2017 | Berlin |
| 9,833,357 B2 | 12/2017 | Berlin |
| 9,931,243 B2 | 4/2018 | Wardle et al. |
| 10,159,601 B2 | 12/2018 | Berlin |
| 10,335,314 B2 | 7/2019 | Berlin |
| 10,363,168 B2 | 7/2019 | Schieber et al. |
| 10,390,993 B1 | 8/2019 | Berlin |
| 10,406,025 B2 | 9/2019 | Wardle et al. |
| 10,492,949 B2 | 12/2019 | Wardle et al. |
| 10,537,474 B2 | 1/2020 | Euteneuer et al. |
| 10,617,558 B2 | 4/2020 | Schieber et al. |
| 2001/0002438 A1 | 5/2001 | Sepetka et al. |
| 2001/0021835 A1 | 9/2001 | Mitchell et al. |
| 2002/0003546 A1 | 1/2002 | Mochimaru et al. |
| 2002/0013546 A1 | 1/2002 | Grieshaber et al. |
| 2002/0013553 A1 | 1/2002 | Pajunk et al. |
| 2002/0013572 A1 | 1/2002 | Berlin |
| 2002/0052653 A1 | 5/2002 | Durgin |
| 2002/0072673 A1 | 6/2002 | Yamamoto et al. |
| 2002/0082591 A1 | 6/2002 | Haefliger |
| 2002/0133168 A1 | 9/2002 | Smedley et al. |
| 2002/0143284 A1 | 10/2002 | Tu et al. |
| 2002/0165504 A1 | 11/2002 | Sharp et al. |
| 2002/0165522 A1 | 11/2002 | Holmen |
| 2002/0193805 A1 | 12/2002 | Ott et al. |
| 2003/0004457 A1 | 1/2003 | Andersson |
| 2003/0014092 A1 | 1/2003 | Neuhann |
| 2003/0040754 A1 | 2/2003 | Mitchell et al. |
| 2003/0055372 A1 | 3/2003 | Lynch et al. |
| 2003/0060748 A1 | 3/2003 | Baikoff |
| 2003/0060752 A1 | 3/2003 | Bergheim et al. |
| 2003/0060784 A1 | 3/2003 | Hilgers et al. |
| 2003/0093084 A1 | 5/2003 | Nissan et al. |
| 2003/0097151 A1 | 5/2003 | Smedley et al. |
| 2003/0105456 A1 | 6/2003 | Lin |
| 2003/0125351 A1 | 7/2003 | Azuma et al. |
| 2003/0175324 A1 | 9/2003 | Robinson et al. |
| 2003/0181848 A1 | 9/2003 | Bergheim et al. |
| 2003/0187384 A1 | 10/2003 | Bergheim |
| 2003/0212387 A1 | 11/2003 | Kurtz et al. |
| 2003/0229303 A1 | 12/2003 | Haffner et al. |
| 2003/0236483 A1 | 12/2003 | Ren |
| 2003/0236484 A1 | 12/2003 | Lynch et al. |
| 2004/0024345 A1 | 2/2004 | Gharib et al. |
| 2004/0024453 A1 | 2/2004 | Castillejos |
| 2004/0030302 A1 | 2/2004 | Kamata et al. |
| 2004/0070761 A1 | 4/2004 | Horvath et al. |
| 2004/0082939 A1 | 4/2004 | Berlin |
| 2004/0088048 A1 | 5/2004 | Richter et al. |
| 2004/0092856 A1 | 5/2004 | Dahan |
| 2004/0098124 A1 | 5/2004 | Freeman et al. |
| 2004/0102729 A1 | 5/2004 | Haffner et al. |
| 2004/0106975 A1 | 6/2004 | Solovay et al. |
| 2004/0111050 A1 | 6/2004 | Smedley et al. |
| 2004/0116909 A1 | 6/2004 | Neuberger et al. |
| 2004/0122380 A1 | 6/2004 | Utterberg |
| 2004/0127843 A1 | 7/2004 | Tu et al. |
| 2004/0147870 A1 | 7/2004 | Burns et al. |
| 2004/0193095 A1 | 9/2004 | Shadduck |
| 2004/0193262 A1 | 9/2004 | Shadduck |
| 2004/0199149 A1 | 10/2004 | Myers et al. |
| 2004/0199171 A1 | 10/2004 | Akahoshi |
| 2004/0210181 A1 | 10/2004 | Vass et al. |
| 2004/0210185 A1 | 10/2004 | Tu et al. |
| 2004/0216749 A1 | 11/2004 | Tu |
| 2004/0225357 A1 | 11/2004 | Worst et al. |
| 2004/0228013 A1 | 11/2004 | Goldstein et al. |
| 2004/0249333 A1 | 12/2004 | Bergheim |

(56) References Cited

U.S. PATENT DOCUMENTS

| | | |
|---|---|---|
| 2004/0254517 A1 | 12/2004 | Quiroz-Mercado et al. |
| 2004/0254519 A1 | 12/2004 | Tu et al. |
| 2004/0254520 A1 | 12/2004 | Porteous et al. |
| 2004/0260228 A1 | 12/2004 | Lynch et al. |
| 2005/0041200 A1 | 2/2005 | Rich |
| 2005/0043722 A1 | 2/2005 | Lin |
| 2005/0049578 A1 | 3/2005 | Tu et al. |
| 2005/0090806 A1 | 4/2005 | Lynch et al. |
| 2005/0090807 A1 | 4/2005 | Lynch et al. |
| 2005/0101967 A1 | 5/2005 | Weber et al. |
| 2005/0107734 A1 | 5/2005 | Coroneo |
| 2005/0119601 A9 | 6/2005 | Lynch et al. |
| 2005/0119636 A1 | 6/2005 | Haffner et al. |
| 2005/0125003 A1 | 6/2005 | Pinchuk et al. |
| 2005/0131514 A1 | 6/2005 | Hijlkema et al. |
| 2005/0149114 A1 | 7/2005 | Cartledge et al. |
| 2005/0154443 A1 | 7/2005 | Linder et al. |
| 2005/0165385 A1 | 7/2005 | Simon |
| 2005/0192527 A1 | 9/2005 | Gharib et al. |
| 2005/0197667 A1 | 9/2005 | Chan et al. |
| 2005/0203542 A1 | 9/2005 | Weber et al. |
| 2005/0209549 A1 | 9/2005 | Bergheim |
| 2005/0209550 A1 | 9/2005 | Bergheim |
| 2005/0240168 A1 | 10/2005 | Neuberger et al. |
| 2005/0244464 A1 | 11/2005 | Hughes |
| 2005/0245916 A1 | 11/2005 | Connor |
| 2005/0250788 A1 | 11/2005 | Tu et al. |
| 2005/0260186 A1 | 11/2005 | Bookbinder et al. |
| 2005/0266047 A1 | 12/2005 | Tu et al. |
| 2005/0271704 A1 | 12/2005 | Tu et al. |
| 2005/0273033 A1 | 12/2005 | Grahn et al. |
| 2005/0277864 A1 | 12/2005 | Haffner et al. |
| 2005/0279369 A1 | 12/2005 | Lin |
| 2005/0288619 A1 | 12/2005 | Gharib et al. |
| 2005/0288745 A1 | 12/2005 | Andersen et al. |
| 2006/0020247 A1 | 1/2006 | Kagan et al. |
| 2006/0021623 A1 | 2/2006 | Miller et al. |
| 2006/0032507 A1 | 2/2006 | Tu |
| 2006/0052879 A1 | 3/2006 | Kolb |
| 2006/0069340 A1 | 3/2006 | Simon |
| 2006/0074375 A1 | 4/2006 | Bergheim |
| 2006/0079828 A1 | 4/2006 | Brown |
| 2006/0084907 A1 | 4/2006 | Bergheim |
| 2006/0084954 A1 | 4/2006 | Zadoyan et al. |
| 2006/0106370 A1 | 5/2006 | Baerveldt et al. |
| 2006/0110428 A1 | 5/2006 | Dejuan et al. |
| 2006/0116626 A1 | 6/2006 | Smedley et al. |
| 2006/0129141 A1 | 6/2006 | Lin |
| 2006/0149194 A1 | 7/2006 | Conston et al. |
| 2006/0154981 A1 | 7/2006 | Klimko et al. |
| 2006/0155238 A1 | 7/2006 | Shields |
| 2006/0155265 A1 | 7/2006 | Juhasz et al. |
| 2006/0155300 A1 | 7/2006 | Stamper et al. |
| 2006/0167421 A1 | 7/2006 | Quinn |
| 2006/0167466 A1 | 7/2006 | Dusek |
| 2006/0173397 A1 | 8/2006 | Tu et al. |
| 2006/0173399 A1 | 8/2006 | Rodgers et al. |
| 2006/0178674 A1 | 8/2006 | Mcintyre |
| 2006/0189915 A1 | 8/2006 | Camras et al. |
| 2006/0189916 A1 | 8/2006 | Bas |
| 2006/0189917 A1 | 8/2006 | Mayr et al. |
| 2006/0195055 A1 | 8/2006 | Bergheim |
| 2006/0195056 A1 | 8/2006 | Bergheim |
| 2006/0195187 A1 | 8/2006 | Stegmann et al. |
| 2006/0200113 A1 | 9/2006 | Haffner et al. |
| 2006/0224146 A1 | 10/2006 | Lin |
| 2006/0241749 A1 | 10/2006 | Tu et al. |
| 2006/0259021 A1 | 11/2006 | Lin |
| 2006/0264971 A1 | 11/2006 | Akahoshi |
| 2006/0276759 A1 | 12/2006 | Kinast et al. |
| 2007/0010827 A1 | 1/2007 | Tu et al. |
| 2007/0021725 A1* | 1/2007 | Villette ............... A61M 5/3286 604/272 |
| 2007/0027452 A1 | 2/2007 | Varner et al. |
| 2007/0073275 A1 | 3/2007 | Conston et al. |
| 2007/0088432 A1 | 4/2007 | Solovay et al. |
| 2007/0093794 A1 | 4/2007 | Wang et al. |
| 2007/0093796 A1 | 4/2007 | Raksi et al. |
| 2007/0106200 A1 | 5/2007 | Levy |
| 2007/0106236 A1 | 5/2007 | Coroneo |
| 2007/0112292 A1 | 5/2007 | Tu et al. |
| 2007/0118147 A1 | 5/2007 | Smedley et al. |
| 2007/0121120 A1 | 5/2007 | Schachar |
| 2007/0135681 A1 | 6/2007 | Chin et al. |
| 2007/0173791 A1 | 7/2007 | Raksi |
| 2007/0179520 A1 | 8/2007 | West |
| 2007/0191863 A1 | 8/2007 | De Juan et al. |
| 2007/0202186 A1 | 8/2007 | Yamamoto et al. |
| 2007/0208325 A1 | 9/2007 | Kurtz |
| 2007/0219509 A1 | 9/2007 | Tashiro et al. |
| 2007/0219541 A1 | 9/2007 | Kurtz |
| 2007/0235543 A1 | 10/2007 | Zadoyan et al. |
| 2007/0236771 A1 | 10/2007 | Zadoyan et al. |
| 2007/0265582 A1 | 11/2007 | Kaplan et al. |
| 2007/0270945 A1 | 11/2007 | Kobayashi et al. |
| 2007/0276315 A1 | 11/2007 | Haffner et al. |
| 2007/0276316 A1 | 11/2007 | Haffner et al. |
| 2007/0282244 A1 | 12/2007 | Tu et al. |
| 2007/0282245 A1 | 12/2007 | Tu et al. |
| 2007/0293807 A1 | 12/2007 | Lynch et al. |
| 2007/0293872 A1 | 12/2007 | Peyman |
| 2007/0298068 A1 | 12/2007 | Badawi et al. |
| 2008/0015488 A1 | 1/2008 | Tu et al. |
| 2008/0027519 A1 | 1/2008 | Guerrero |
| 2008/0045878 A1 | 2/2008 | Bergheim |
| 2008/0058704 A1 | 3/2008 | Hee et al. |
| 2008/0058777 A1 | 3/2008 | Kurtz et al. |
| 2008/0082088 A1 | 4/2008 | Kurtz et al. |
| 2008/0091224 A1 | 4/2008 | Griffis et al. |
| 2008/0119827 A1 | 5/2008 | Kurtz et al. |
| 2008/0228127 A1 | 9/2008 | Burns et al. |
| 2008/0278687 A1 | 11/2008 | Somani |
| 2008/0288082 A1 | 11/2008 | Deal |
| 2008/0312661 A1 | 12/2008 | Downer et al. |
| 2009/0005852 A1 | 1/2009 | Gittings et al. |
| 2009/0028953 A1 | 1/2009 | Yamamoto et al. |
| 2009/0030363 A1 | 1/2009 | Gellman |
| 2009/0030381 A1 | 1/2009 | Lind et al. |
| 2009/0036843 A1 | 2/2009 | Erskine |
| 2009/0043321 A1 | 2/2009 | Conston et al. |
| 2009/0054723 A1 | 2/2009 | Khairkhahan et al. |
| 2009/0069786 A1 | 3/2009 | Vesely et al. |
| 2009/0082860 A1 | 3/2009 | Schieber et al. |
| 2009/0082862 A1 | 3/2009 | Schieber et al. |
| 2009/0104248 A1 | 4/2009 | Rapacki et al. |
| 2009/0118716 A1 | 5/2009 | Brownell |
| 2009/0118717 A1 | 5/2009 | Brownell et al. |
| 2009/0118718 A1 | 5/2009 | Raksi et al. |
| 2009/0131885 A1* | 5/2009 | Akahoshi ............... A61M 1/84 604/272 |
| 2009/0131921 A1 | 5/2009 | Kurtz et al. |
| 2009/0137988 A1 | 5/2009 | Kurtz |
| 2009/0138081 A1 | 5/2009 | Bergheim et al. |
| 2009/0157062 A1 | 6/2009 | Hauger et al. |
| 2009/0171327 A1 | 7/2009 | Kurtz et al. |
| 2009/0182421 A1 | 7/2009 | Silvestrini et al. |
| 2009/0198248 A1 | 8/2009 | Yeung et al. |
| 2009/0204053 A1 | 8/2009 | Nissan et al. |
| 2009/0247955 A1 | 10/2009 | Yamamoto et al. |
| 2009/0259126 A1 | 10/2009 | Saal et al. |
| 2009/0281520 A1 | 11/2009 | Highley et al. |
| 2009/0281530 A1 | 11/2009 | Korn |
| 2009/0291423 A1 | 11/2009 | Hara |
| 2010/0004580 A1 | 1/2010 | Lynch et al. |
| 2010/0036488 A1 | 2/2010 | De Juan et al. |
| 2010/0057072 A1 | 3/2010 | Roman et al. |
| 2010/0114309 A1 | 5/2010 | De Juan et al. |
| 2010/0121342 A1* | 5/2010 | Schieber ............... A61M 31/00 606/108 |
| 2010/0137981 A1 | 6/2010 | Silvestrini et al. |
| 2010/0173866 A1 | 7/2010 | Hee et al. |
| 2010/0191176 A1 | 7/2010 | Ho et al. |
| 2010/0191177 A1 | 7/2010 | Chang et al. |
| 2010/0234726 A1 | 9/2010 | Sirimanne et al. |

(56) References Cited

U.S. PATENT DOCUMENTS

| | | |
|---|---|---|
| 2010/0234790 A1 | 9/2010 | Tu et al. |
| 2010/0262174 A1 | 10/2010 | Sretavan et al. |
| 2010/0274258 A1 | 10/2010 | Silvestrini et al. |
| 2010/0324543 A1 | 12/2010 | Kurtz et al. |
| 2010/0331858 A1 | 12/2010 | Simaan et al. |
| 2011/0009874 A1 | 1/2011 | Wardle et al. |
| 2011/0028948 A1 | 2/2011 | Raksi et al. |
| 2011/0028949 A1 | 2/2011 | Raksi et al. |
| 2011/0028950 A1 | 2/2011 | Raksi et al. |
| 2011/0028951 A1 | 2/2011 | Raksi et al. |
| 2011/0028952 A1 | 2/2011 | Raksi et al. |
| 2011/0028953 A1 | 2/2011 | Raksi et al. |
| 2011/0028954 A1 | 2/2011 | Raksi et al. |
| 2011/0028955 A1 | 2/2011 | Raksi |
| 2011/0028957 A1 | 2/2011 | Raksi et al. |
| 2011/0028958 A1 | 2/2011 | Raksi et al. |
| 2011/0098809 A1 | 4/2011 | Wardle et al. |
| 2011/0196487 A1 | 8/2011 | Badawi et al. |
| 2011/0218523 A1 | 9/2011 | Rob |
| 2011/0224597 A1 | 9/2011 | Stegmann et al. |
| 2011/0319806 A1 | 12/2011 | Wardle |
| 2012/0010702 A1 | 1/2012 | Stegmann et al. |
| 2012/0021397 A1 | 1/2012 | Van Dalen et al. |
| 2012/0022424 A1 | 1/2012 | Yamamoto et al. |
| 2012/0035524 A1 | 2/2012 | Silvestrini |
| 2012/0191064 A1 | 7/2012 | Conston et al. |
| 2012/0271272 A1 | 10/2012 | Hammack et al. |
| 2012/0283557 A1 | 11/2012 | Berlin |
| 2012/0302861 A1 | 11/2012 | Marshall et al. |
| 2013/0023837 A1 | 1/2013 | Becker |
| 2013/0150959 A1 | 6/2013 | Schieber et al. |
| 2013/0158462 A1 | 6/2013 | Wardle et al. |
| 2013/0182223 A1 | 7/2013 | Wardle et al. |
| 2013/0184631 A1 | 7/2013 | Pinchuk |
| 2013/0231603 A1 | 9/2013 | Wardle et al. |
| 2013/0253402 A1 | 9/2013 | Badawi et al. |
| 2013/0253403 A1 | 9/2013 | Badawi et al. |
| 2013/0253437 A1 | 9/2013 | Badawi et al. |
| 2013/0253438 A1 | 9/2013 | Badawi et al. |
| 2013/0253528 A1 | 9/2013 | Haffner et al. |
| 2013/0267887 A1 | 10/2013 | Kahook et al. |
| 2013/0281907 A1 | 10/2013 | Wardle et al. |
| 2013/0281908 A1 | 10/2013 | Schaller et al. |
| 2014/0018720 A1 | 1/2014 | Horvath et al. |
| 2014/0066821 A1 | 3/2014 | Friedland et al. |
| 2014/0066831 A1 | 3/2014 | Silvestrini et al. |
| 2014/0081195 A1 | 3/2014 | Clauson et al. |
| 2014/0114229 A1 | 4/2014 | Wardle et al. |
| 2014/0249463 A1 | 9/2014 | Wardle et al. |
| 2015/0018746 A1 | 1/2015 | Hattenbach |
| 2015/0022780 A1 | 1/2015 | John et al. |
| 2015/0038893 A1 | 2/2015 | Haffner et al. |
| 2015/0045714 A1 | 2/2015 | Horvath et al. |
| 2015/0057583 A1 | 2/2015 | Gunn et al. |
| 2015/0057591 A1 | 2/2015 | Horvath et al. |
| 2015/0065940 A1 | 3/2015 | Rangel-Friedman et al. |
| 2015/0080783 A1 | 3/2015 | Berlin |
| 2015/0119787 A1 | 4/2015 | Wardle et al. |
| 2015/0148836 A1 | 5/2015 | Heeren |
| 2015/0223983 A1 | 8/2015 | Schieber et al. |
| 2015/0223984 A1 | 8/2015 | Schieber et al. |
| 2015/0223985 A1 | 8/2015 | Schieber et al. |
| 2015/0250649 A1 | 9/2015 | Euteneuer et al. |
| 2015/0282982 A1 | 10/2015 | Schieber et al. |
| 2015/0290033 A1 | 10/2015 | Wardle et al. |
| 2015/0305939 A1 | 10/2015 | Vera et al. |
| 2015/0305940 A1 | 10/2015 | Vera et al. |
| 2015/0313759 A1 | 11/2015 | Vera et al. |
| 2015/0366710 A1 | 12/2015 | Schieber et al. |
| 2016/0051406 A1 | 2/2016 | Wardle et al. |
| 2016/0220417 A1 | 8/2016 | Schieber et al. |
| 2016/0250072 A1 | 9/2016 | Wardle et al. |
| 2017/0143541 A1 | 5/2017 | Badawi et al. |
| 2017/0156848 A1 | 6/2017 | Schieber |
| 2017/0172794 A1 | 6/2017 | Varner et al. |
| 2017/0172795 A1 | 6/2017 | Lerner |
| 2017/0172797 A1 | 6/2017 | Horvath et al. |
| 2017/0172798 A1 | 6/2017 | Horvath et al. |
| 2017/0172799 A1 | 6/2017 | Horvath |
| 2017/0172800 A1 | 6/2017 | Romoda et al. |
| 2017/0202708 A1 | 7/2017 | Berlin |
| 2017/0239272 A1 | 8/2017 | Ambati et al. |
| 2017/0281409 A1 | 10/2017 | Haffner et al. |
| 2017/0290705 A1 | 10/2017 | Wardle et al. |
| 2017/0360609 A9 | 12/2017 | Schieber et al. |
| 2018/0369017 A1 | 12/2018 | Schieber et al. |
| 2019/0076296 A1 | 3/2019 | Van Meter et al. |
| 2019/0343679 A1 | 11/2019 | Wardle et al. |
| 2019/0380873 A1 | 12/2019 | Berlin |
| 2019/0380874 A1 | 12/2019 | Schieber et al. |
| 2020/0060876 A1 | 2/2020 | Wardle et al. |
| 2020/0085620 A1 | 3/2020 | Euteneuer et al. |
| 2020/0197221 A1 | 6/2020 | Schieber et al. |
| 2020/0222238 A1 | 7/2020 | Schieber et al. |
| 2020/0261270 A1 | 8/2020 | Berlin |
| 2021/0030590 A1 | 2/2021 | Blanda et al. |
| 2021/0330499 A1 | 10/2021 | Wardle et al. |
| 2021/0361479 A1 | 11/2021 | Wardle et al. |
| 2022/0054314 A1 | 2/2022 | Van Meter et al. |
| 2022/0096271 A1 | 3/2022 | Wardle et al. |

FOREIGN PATENT DOCUMENTS

| | | | |
|---|---|---|---|
| DE | 4226476 | 8/1993 | |
| DE | 4235483 A1 * | 4/1994 | ........... A61B 5/1405 |
| DE | 102012221350 | 5/2014 | |
| EP | 0168201 | 6/1988 | |
| EP | 0766544 | 5/1998 | |
| EP | 0957949 | 8/2004 | |
| EP | 1715827 | 11/2006 | |
| EP | 1615604 | 8/2009 | |
| EP | 2193821 | 6/2010 | |
| EP | 2380622 | 10/2011 | |
| EP | 2468327 | 6/2012 | |
| EP | 2471563 | 7/2012 | |
| EP | 1833440 | 8/2012 | |
| EP | 2996648 | 6/2017 | |
| EP | 1732484 | 8/2017 | |
| EP | 1740153 | 8/2017 | |
| EP | 3205333 | 10/2018 | |
| JP | 10-504978 | 5/1998 | |
| JP | 11-123205 | 5/1999 | |
| JP | 2002-542872 | 12/2002 | |
| JP | 2006-289075 | 10/2006 | |
| JP | 2006-517848 | 3/2007 | |
| JP | 2009-523545 | 6/2009 | |
| JP | 2010-509003 | 1/2011 | |
| JP | 2011-502649 | 12/2011 | |
| JP | 2012-527318 | 11/2012 | |
| JP | 2015-517836 | 5/2016 | |
| WO | WO 1996/020742 | 7/1996 | |
| WO | WO 1999/001063 | 1/1999 | |
| WO | WO 1999/045868 | 9/1999 | |
| WO | WO 2000/007525 | 2/2000 | |
| WO | WO 2000/064389 | 11/2000 | |
| WO | WO 2000/064393 | 11/2000 | |
| WO | WO 2000/067687 | 11/2000 | |
| WO | WO 2001/097727 | 12/2001 | |
| WO | WO 2002/036052 | 5/2002 | |
| WO | WO 2001/089437 | 8/2002 | |
| WO | WO 2002/074052 | 5/2003 | |
| WO | WO 2003/015659 | 5/2003 | |
| WO | WO 2003/045290 | 6/2003 | |
| WO | WO 2002/080811 | 3/2004 | |
| WO | WO 2004/054643 | 7/2004 | |
| WO | WO 2004/093761 | 11/2004 | |
| WO | WO 2005/105197 | 4/2006 | |
| WO | WO 2006/066103 | 10/2006 | |
| WO | WO 2007/047744 | 8/2007 | |
| WO | WO 2007/035356 | 12/2007 | |
| WO | WO 2007/087061 | 12/2007 | |
| WO | WO 2008/002377 | 1/2008 | |
| WO | WO 2008/005873 | 1/2008 | |
| WO | WO 2009/120960 | 12/2009 | |

(56) References Cited

FOREIGN PATENT DOCUMENTS

| WO | WO 2011/053512 | 5/2011 |
|---|---|---|
| WO | WO 2011/057283 | 5/2011 |
| WO | WO 2011/106781 | 9/2011 |
| WO | WO 2011/150045 | 12/2011 |
| WO | WO 2012/051575 | 6/2012 |
| WO | WO 2012/083143 | 6/2012 |
| WO | WO 2013/147978 | 10/2013 |

OTHER PUBLICATIONS

Cambridge Dictionary; Sensor (definition); 2 pages; retrived from the internet (http://dictionary.cambridge.org/define.asp?dict=CALD&key=71811>) on Aug. 14, 2018.
Camras et al., "A novel schlemm's canal scaffold increases outflow facility in a human anterior segment perfusion model," Invest. Opthalmol. Vis Sci., vol. 53(10), pp. 6115-6121. Sep. 1, 2012.
D'Ermo, et al., "Our results with the operation of ab externo trabeculotomy," Ophthalmologica, vol. 163; pp. 347-355; 1971.
Dietlein et al., "Morphological variability of the trabecular meshwork in glaucoma patients: implications for non-perforating glaucoma surgery," British Journal of Ophthalmology, vol. 84(12), pp. 1354-1359; Dec. 1, 2000.
Ellingsen et al., "Trabeculotomy and sinusotomy in enucleated human eyes," Investigative Ophthalmology, vol. 11; pp. 21-28; Jan. 1972.
Grant, "Experimental aqueous perfusion in enucleated human eyes," Archives of Ophthalmology, vol. 69, pp. 783-801, Jun. 1963.
Gulati et al., "A novel 8-mm schlemm's canal scaffold reduces outflow resistance in a human anterior segment perfusion model," Investigative Ophthalmology & Visual Science, vol. 54(3), pp. 1698-1704, Mar. 5, 2013.
Huang et al., "Optical coherence tomography," Science, vol. 254(5035), pp. 1178-1181, 12 pages (Author Manuscript), Nov. 1991.
Johnstone et al., "Microsurgery of Schlemm's Canal and the Human Aqueous Outflow System;" American Journal of Ophthalmology, vol. 76 (6), pp. 906-917, Dec. 1973.
Johnstone, "Aqueous humor outflow system overview," Becker-Shaffer's Diagnosis and Therapy of the Glaucomas, Part 2 Aqueous Humor Dynamics; Chapter 3; pp. 25-46; Mosby Eiseveir, Edition 8, Jun. 2009.
Kirkness et al., "The Use of Silicone Drainage Tubing to Control Post-Keratoplasty Glaucoma," Eye, 2 (pt 5), pp. 583-590, Apr. 1988.
Lee et al. "Aqueous-venous shunt and intraocular pressure. Preliminary report of animal studies," Investigative Ophthalmology, vol. 5 No. 1: 59-64, Feb. 1966.
Lee et al., "Short-pulsed neodymium—YAG laser trabeculotomy. An in vivo morphological study in the human eye," Investigative Ophthalmology and Visual Science, vol. 29(11), pp. 1698-1707, Nov. 1988.
Macmilla Online Dictionary: Detector (definition): Macmilla On Line Dictionary, 2 pages, retrieved from the internet (https://www.macmillandictionary.com/dictionary/british/detector) on Aug. 14, 2018.
Maepea et al., "The pressures in the episcleral veins, schlemm's canal and the trabecular meshwork in monkeys: effects of changes in intraocular pressure," Exp. Eye Res., vol. 49 (4), pp. 645-663, Oct. 1989.
Molteno et al., "Long Tube Implants in the Management of Glaucoma," SA Medical Journal, vol. 26; pp. 1062-1066, Jun. 1976.
Molteno, "New implant for drainage in glaucoma," Brit. J. Ophthal, vol. 53, pp. 606-615, Sep. 1969.
Moses, R., "The effect of intraocular pressure on resistance to outflow," Survey of Ophthalmology, vol. 22, No. 2, pp. 88-100, Sep.-Oct. 1977.
Nakamura et al., "Femtosecond laser photodisruption of primate trabecular rneshwork: an ex vivo study," Investigative Ophthalmology and Visual Science, vol. 50(3), pp. 1198-1204, Mar. 2009.
Owen, "A moving-mirror gonioscope for retinal surgery," British Journal of Ophthalmology, vol. 61(3), pp. 246-247, Mar. 1977.
Oxford Dictionaries: Detector (definition); 1 page; retrieved from the internet (https://en.oxforddictionaries.com/definition/detector) on Aug. 14, 2018.
Oxford Dictionaries: Sensor (definition); 1 page; retrieved from the internet (http://www.askoxford.com/concise_oed/sensor?view=uk>) on Aug. 14, 2018.
Radhakrishnan et al., "Real-time optical coherence tomography of the anterior segment at 1310 nm," Archives of Opthhalmology, vol. 119(8); pp. 1179-1185, Aug. 2001.
Rosenquist et al., "Outflow resistance of enucleated human eyes at two different perfusion pressures and different extents of trabeculotomy," Current Eye Res., vol. 8, No. 12, pp. 1233-1240, Dec. 1989.
Savage, J., "Gonioscopy in the management of glaucoma," Focal Points: Am. Academy of Ophthalmology, vol. 24, No. 3, pp. 1-14; Mar. 2006.
Schocket et al., "Anterior Chamber Tube Shunt to an Encircling Band in theTreatment of Neovascular Glaucoma and other Refractory Glaucomas," Ophthalmology, vol. 92, pp. 553-562, Apr. 1985.
Schultz, J., "Canaloplasty procedure shows promise for open-angle glaucoma in European study," Ocular Surgery News, vol. 34, Mar. 1, 2007.
Smit et al., "Effects of viscoelastic injection into schlemm's canal in primate and human eyes," J. Am. Academy of Ophthalmology, vol. 109(4), pp. 786-792, April 20002.
Spiegel et al., "Schlemm's canal implant: a new method to lower intraocular pressure in patients with POAG?," Ophthalmic Surgery and Lasers, vol. 30(6), pp. 492-494; Jun. 1999.
Sugiyama et al., "Micro-Diaphragm Pressure Sensor," 1986 International Electron Devices Meeting, pp. 184-187, Dec. 7, 1986.
Toyran et al., "Femtosecond laser photodisruption of human trabecular rneshwork: an in vitro study," Experimental Eye Research, vol. 81 (3), pp. 298-305, Sep. 2005.
Wilcox et al., "Hypothesis for Improving Accessory Filtration by Using Geometry," Journal of Glaucoma, vol. 3(3), pp. 244-247, Fall 1994.

* cited by examiner

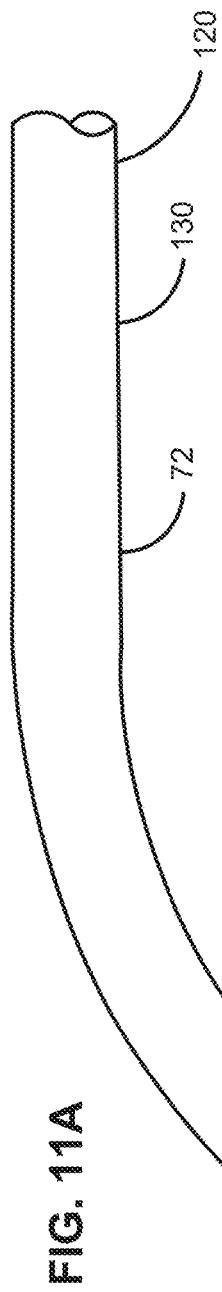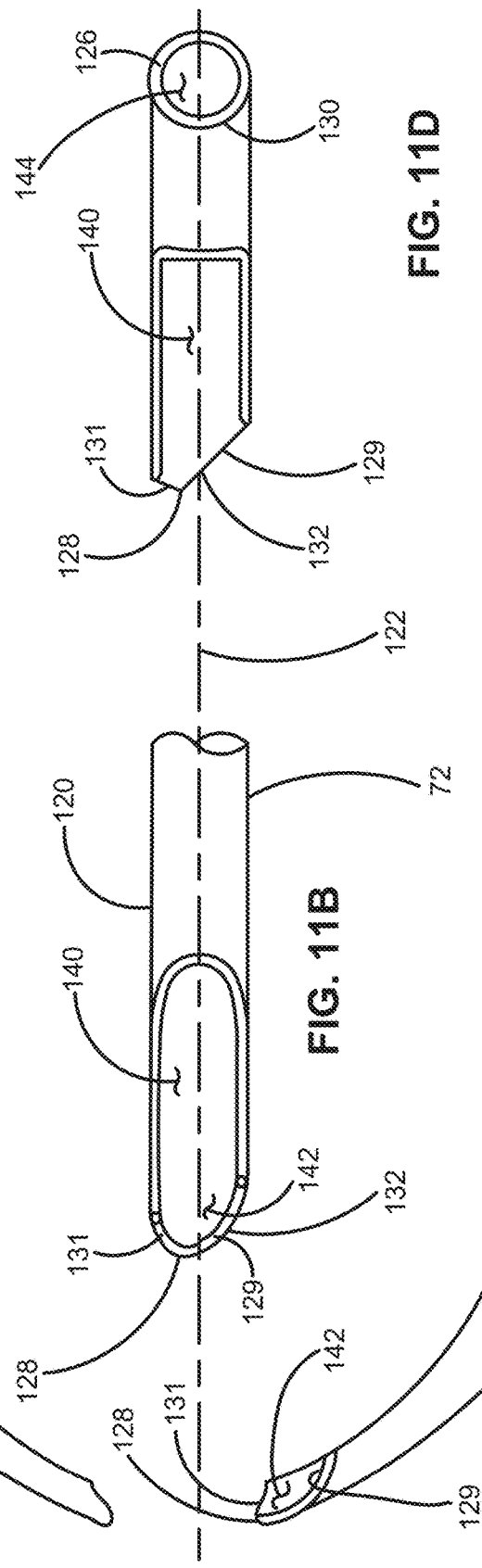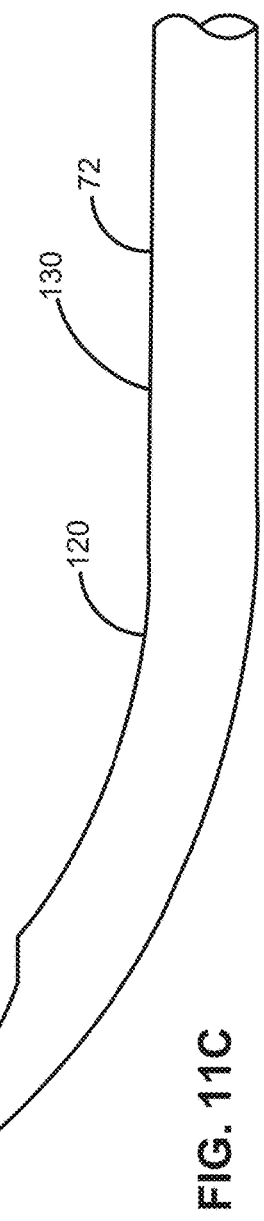
FIG. 11A
FIG. 11B
FIG. 11C
FIG. 11D

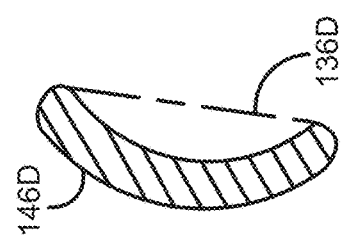
FIG. 12A
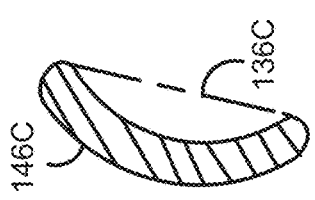
FIG. 12B
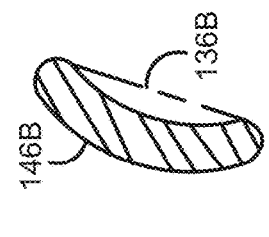
FIG. 12C
FIG. 12D
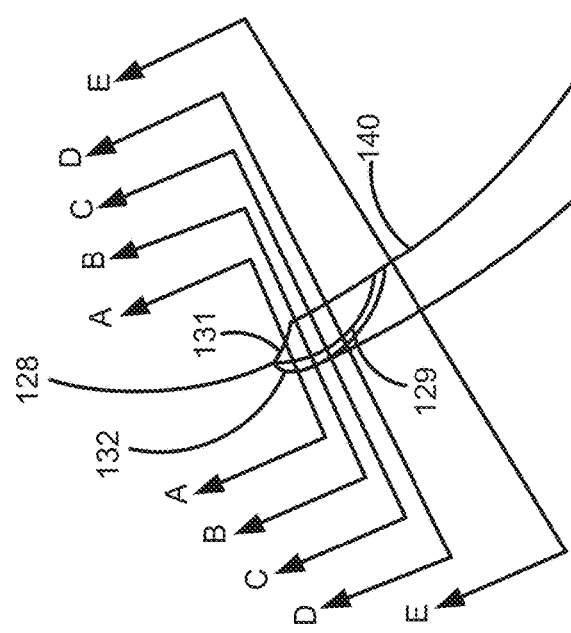
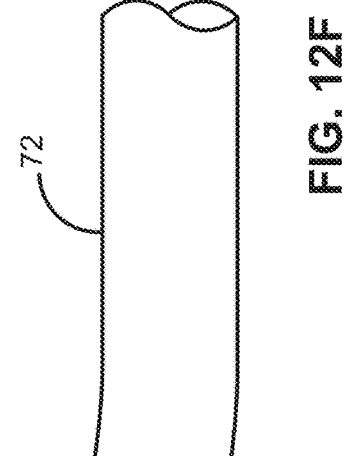
FIG. 12E
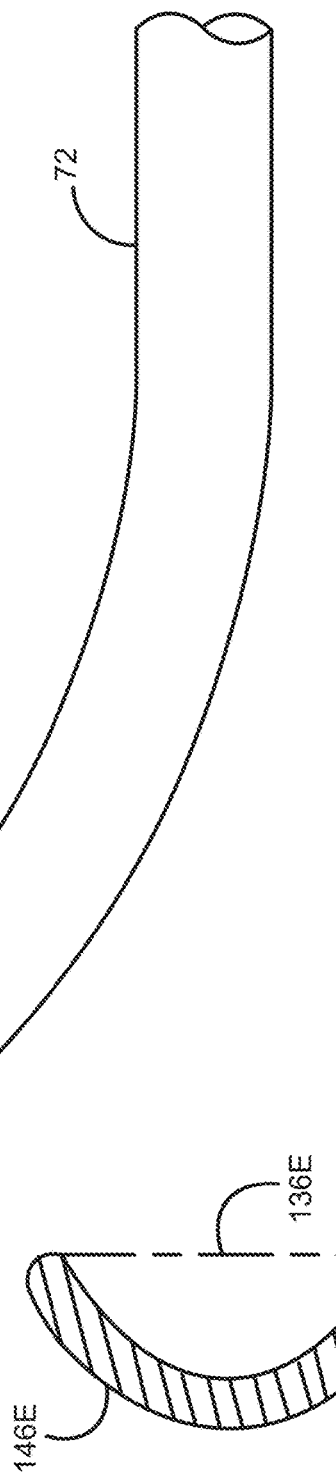
FIG. 12F

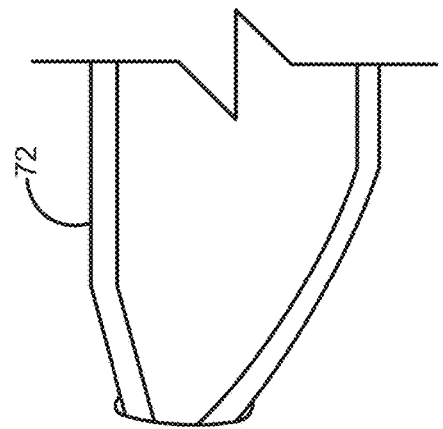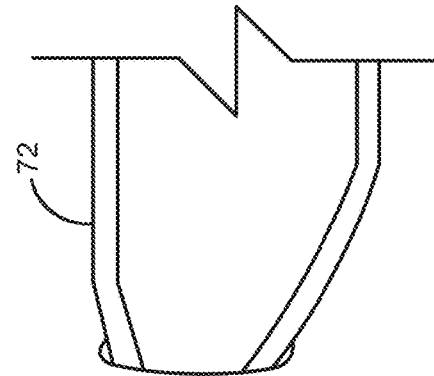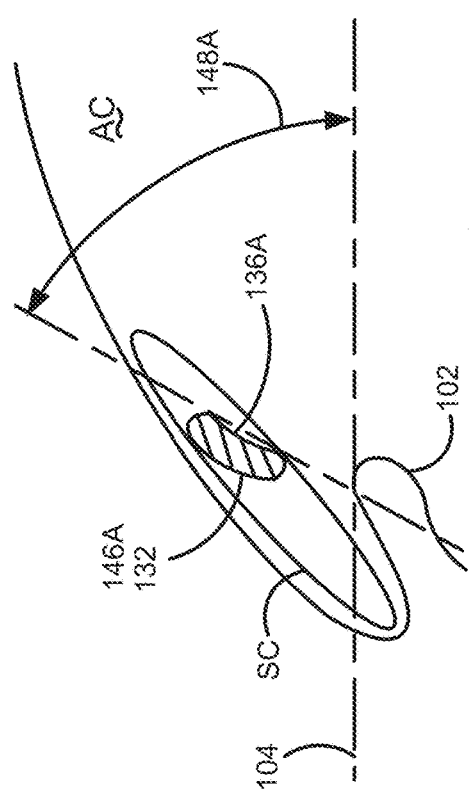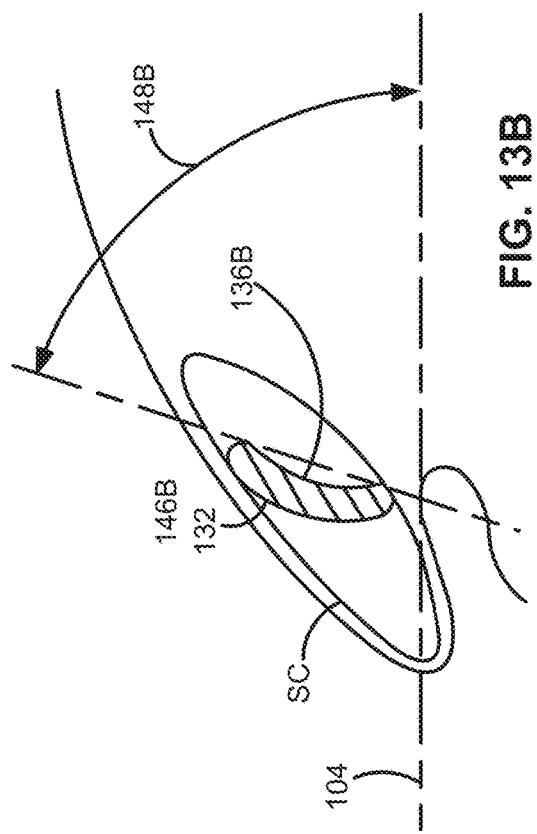

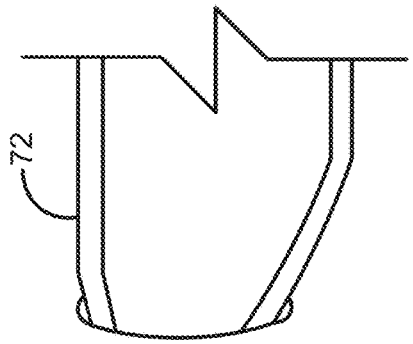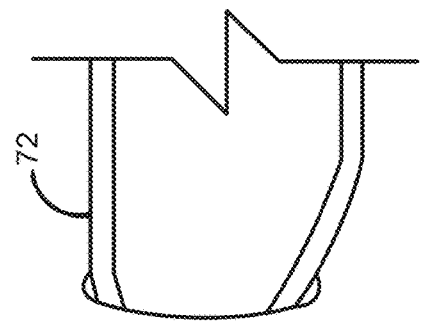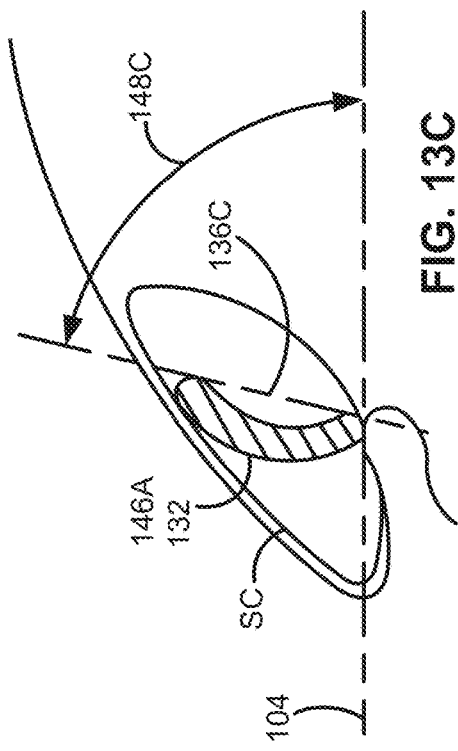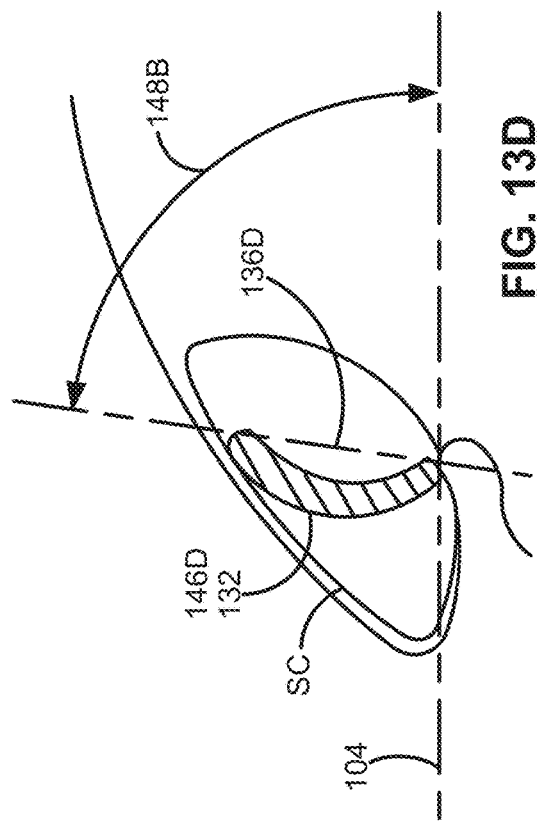

APPARATUS FOR DELIVERING OCULAR IMPLANTS INTO AN ANTERIOR CHAMBER OF THE EYE

CROSS REFERENCE TO RELATED APPLICATIONS

This application is a continuation U.S. patent application Ser. No. 16/805,217, filed Feb. 28, 2020, which is a continuation of U.S. patent application Ser. No. 14/440,610, filed May 5, 2015, now U.S. Pat. No. 10,617,558, which application is the national stage of International Application No. PCT/US2013/072001, filed Nov. 26, 2013, which application claims the benefit of U.S. Provisional Application No. 61/730,895, filed Nov. 28, 2012, the disclosures of which are incorporated by reference in their entirety.

INCORPORATION BY REFERENCE

All publications and patent applications mentioned in this specification are herein incorporated by reference to the same extent as if each individual publication or patent application was specifically and individually indicated to be incorporated by reference.

FIELD

The present disclosure relates generally to devices that are implanted within the eye. More particularly, the present disclosure relates to systems, devices and methods for delivering ocular implants into the eye.

BACKGROUND

According to a draft report by The National Eye Institute (NEI) at The United States National Institutes of Health (NIH), glaucoma is now the leading cause of irreversible blindness worldwide and the second leading cause of blindness, behind cataract, in the world. Thus, the NEI draft report concludes, "it is critical that significant emphasis and resources continue to be devoted to determining the pathophysiology and management of this disease." Glaucoma researchers have found a strong correlation between high intraocular pressure and glaucoma. For this reason, eye care professionals routinely screen patients for glaucoma by measuring intraocular pressure using a device known as a tonometer. Many modem tonometers make this measurement by blowing a sudden puff of air against the outer surface of the eye.

The eye can be conceptualized as a ball filled with fluid. There are two types of fluid inside the eye. The cavity behind the lens is filled with a viscous fluid known as vitreous humor. The cavities in front of the lens are filled with a fluid know as aqueous humor. Whenever a person views an object, he or she is viewing that object through both the vitreous humor and the aqueous humor.

Whenever a person views an object, he or she is also viewing that object through the cornea and the lens of the eye. In order to be transparent, the cornea and the lens can include no blood vessels. Accordingly, no blood flows through the cornea and the lens to provide nutrition to these tissues and to remove wastes from these tissues. Instead, these functions are performed by the aqueous humor. A continuous flow of aqueous humor through the eye provides nutrition to portions of the eye (e.g., the cornea and the lens) that have no blood vessels. This flow of aqueous humor also removes waste from these tissues.

Aqueous humor is produced by an organ known as the ciliary body. The ciliary body includes epithelial cells that continuously secrete aqueous humor. In a healthy eye, a stream of aqueous humor flows out of the anterior chamber of the eye through the trabecular meshwork and into Schlemm's canal as new aqueous humor is secreted by the epithelial cells of the ciliary body. This excess aqueous humor enters the venous blood stream from Schlemm's canal and is carried along with the venous blood leaving the eye.

When the natural drainage mechanisms of the eye stop functioning properly, the pressure inside the eye begins to rise. Researchers have theorized prolonged exposure to high intraocular pressure causes damage to the optic nerve that transmits sensory information from the eye to the brain. This damage to the optic nerve results in loss of peripheral vision. As glaucoma progresses, more and more of the visual field is lost until the patient is completely blind.

In addition to drug treatments, a variety of surgical treatments for glaucoma have been performed. For example, shunts were implanted to direct aqueous humor from the anterior chamber to the extraocular vein (Lee and Scheppens, "Aqueous-venous shunt and intraocular pressure," *Investigative Ophthalmology* (February 1966)). Other early glaucoma treatment implants led from the anterior chamber to a sub-conjunctival bleb (e.g., U.S. Pat. Nos. 4,968,296 and 5,180,362). Still others were shunts leading from the anterior chamber to a point just inside Schlemm's canal (Spiegel et al., "Schlemm's canal implant: a new method to lower intraocular pressure in patients with POAG?" *Ophthalmic Surgery and Lasers* (June 1999); U.S. Pat. Nos. 6,450,984; 6,450,984).

SUMMARY OF THE DISCLOSURE

A cannula for delivering an ocular implant into Schlemm's canal of an eye is provided, comprising a rigid curved tube adapted to extend through an anterior chamber of the eye to achieve tangential entry into Schlemm's canal, a trough portion formed by an opening extending along a distal portion of the rigid curved tube, and an asymmetric tip disposed at a distal end of the trough portion, the asymmetric tip being located at an intersection between an upper camming surface and a lower camming surface, the upper camming surface being configured to contact scleral tissue of the eye to guide the trough portion into Schlemm's canal, the lower camming surface being configured to contact a scleral spur of the eye to guide the trough portion into Schlemm's canal.

In some embodiments, the asymmetric tip is configured to not pierce the scleral tissue. In other embodiments, the asymmetric tip is configured to pierce the trabecular meshwork. In some embodiments, the asymmetric tip is formed by the upper camming surface being shorter than the lower camming surface.

In one embodiment, the rigid curved tube and the trough portion define a path for directing the ocular implant from a location outside of the eye to a location within Schlemm's canal of the eye.

In some embodiments, the asymmetric tip is sufficiently blunt to slide along an outer wall of Schlemm's canal without cutting the scleral tissue underlying the outer wall of Schlemm's canal.

In one embodiment, the asymmetric tip has an asymmetric V-shape.

In some embodiments, the cannula is shaped and dimensioned so that at least part some of the trough portion can be advanced into Schlemm's canal while a first portion of the rigid curved tube is disposed inside the anterior chamber and a second portion of the rigid curved tube is extended through an incision in the eye to a location outside of the eye.

An ocular implant and delivery system is also provided, comprising a rigid curved cannula adapted to extend through an anterior chamber of an eye to achieve tangential entry into Schlemm's canal of the eye, a trough portion formed by an opening extending along a distal portion of the rigid curved cannula, an ocular implant configured to be carried inside the rigid curved cannula and advanced distally through the rigid curved cannula and along the trough portion into Schlemm's canal, and an asymmetric tip disposed at a distal end of the trough portion, the asymmetric tip being located at an intersection between an upper camming surface and a lower camming surface, the upper camming surface being configured to contact scleral tissue of the eye to guide the trough portion into Schlemm's canal, the lower camming surface being configured to contact a scleral spur of the eye to guide the trough portion into Schlemm's canal.

In some embodiments, the asymmetric tip is configured to not pierce the scleral tissue. In other embodiments, the asymmetric tip is configured to pierce the trabecular meshwork. In some embodiments, the asymmetric tip is formed by the upper camming surface being shorter than the lower camming surface.

In one embodiment, the rigid curved tube and the trough portion define a path for directing the ocular implant from a location outside of the eye to a location within Schlemm's canal of the eye.

In some embodiments, the asymmetric tip is sufficiently blunt to slide along an outer wall of Schlemm's canal without cutting the scleral tissue underlying the outer wall of Schlemm's canal.

In one embodiment, the asymmetric tip has an asymmetric V-shape.

In some embodiments, the cannula is shaped and dimensioned so that at least part some of the trough portion can be advanced into Schlemm's canal while a first portion of the rigid curved tube is disposed inside the anterior chamber and a second portion of the rigid curved tube is extended through an incision in the eye to a location outside of the eye.

In some embodiments, the rigid curved cannula and the trough portion define a path for directing the ocular implant from a location outside of the eye to a location within Schlemm's canal of the eye.

In another embodiment, the asymmetric tip is sufficiently blunt to slide along an outer wall of Schlemm's canal without cutting the scleral tissue underlying the outer wall of Schlemm's canal.

In some embodiments, the asymmetric tip has an asymmetric V-shape.

In another embodiment, the rigid curved cannula is shaped and dimensioned so that at least part some of the trough portion can be advanced into Schlemm's canal while a first portion of the rigid curved cannula is disposed inside the anterior chamber and a second portion of the rigid curved cannula is extended through an incision in the eye to a location outside of the eye.

A cannula for delivering an ocular implant into Schlemm's canal of an eye is also provided, comprising a rigid body having a distal curved portion adapted to gain tangential entry into Schlemm's canal, a lumen extending from a proximal end of the body through at least part of the distal curved portion, the lumen being adapted to contain the ocular implant, a trough formed in the distal curved portion, the trough being defined by an opening along the body that provides access to a concave inner surface, and a distal tip at a distal end of the trough, the distal tip being in a position offset from a central axis of the trough.

In some embodiments, the distal tip is formed at an intersection between an upper camming surface and a lower camming surface. In one embodiment, the upper camming surface is smaller than the lower camming surface.

In some embodiments, the distal tip is sufficiently blunt to slide along an outer wall of Schlemm's canal without cutting scleral tissue underlying the outer wall of Schlemm's canal.

A method of inserting an ocular implant into Schlemm's canal of an eye is provided, the method comprising inserting a curved cannula having a distal trough portion through an anterior chamber of the eye to gain tangential entry of the trough portion into Schlemm's canal, allowing an upper camming surface of a distal tip of the distal trough portion to contact scleral tissue of the eye to guide the distal trough portion into Schlemm's canal, allowing a lower camming surface of the distal tip of the distal trough portion to contact a scleral spur of the eye to guide the distal trough portion into Schlemm's canal, and advancing an ocular implant through the curved cannula and along the distal trough portion into Schlemm's canal.

In some embodiments of the cannulas described herein, a diameter of the rigid curved tube is larger than a width of Schlemm's canal. In one embodiment, the diameter of the rigid curved tube is approximately 400-500 microns. In another embodiment, the diameter of the rigid curved tube is approximately 350-550 microns.

BRIEF DESCRIPTION OF THE DRAWINGS

FIGS. 11A-11C are plan views of a cannula created using multiview projection.

FIG. 11D is an axial view further illustrating the cannula shown in FIG. 11A.

FIGS. 12A-12D are lateral cross-sectional views of the tip portion of a cannula.

FIG. 12E is a lateral cross-sectional view of a trough portion of the cannula.

FIG. 12F is a plan view of the cannula including a plurality of section lines.

FIGS. 13A-13D form a sequence of stylized section views illustrating the insertion of the tip portion of a cannula into Schlemm's canal located in the anterior chamber of an eye.

FIGS. 13E-13H form a sequence stylized side plan views further illustrating the insertion of the tip portion into Schlemm's canal.

DETAILED DESCRIPTION

The following detailed description should be read with reference to the drawings in which similar elements in different drawings are numbered the same. The drawings, which are not necessarily to scale, depict illustrative embodiments and are not intended to limit the scope of the invention.

Figure 1:
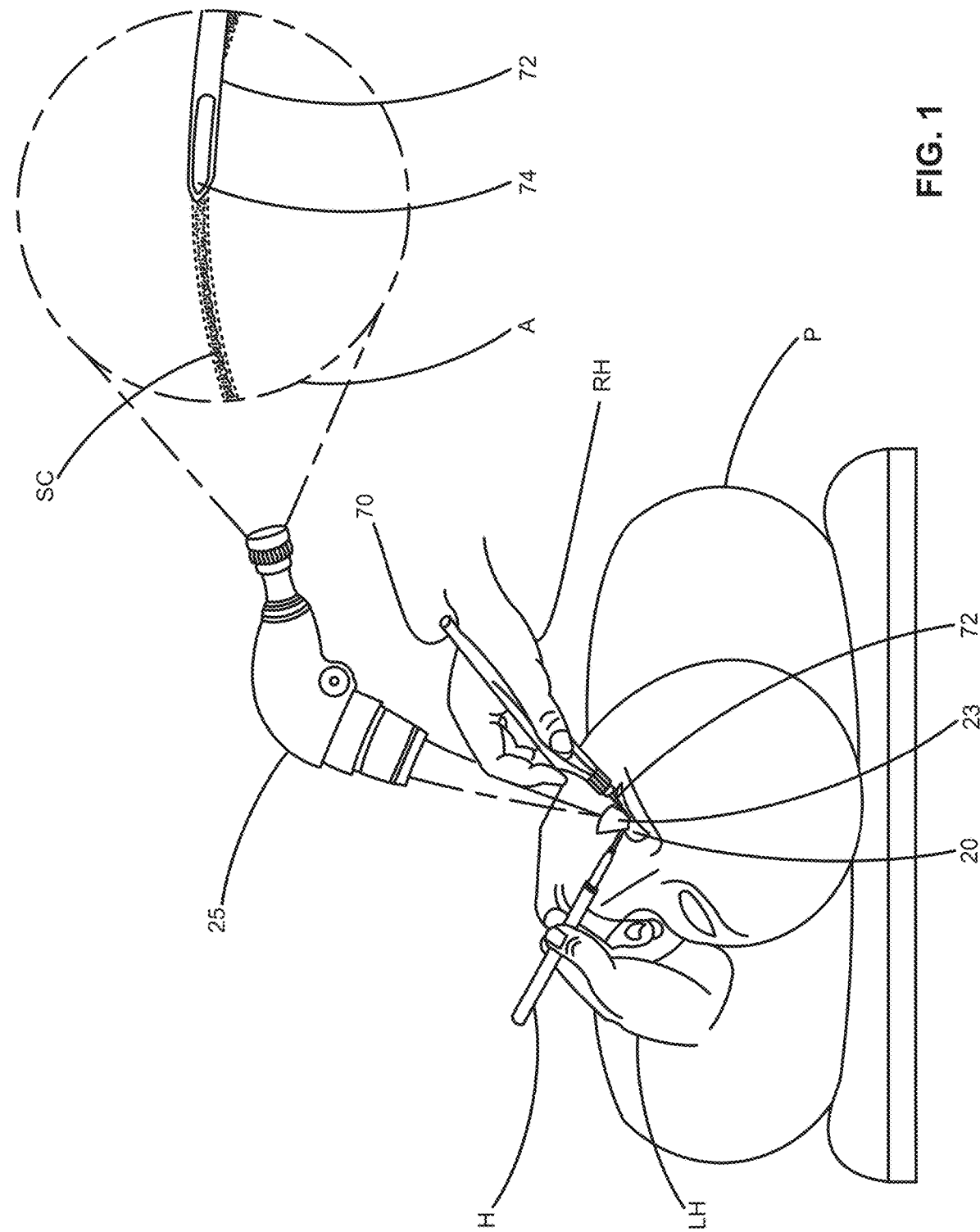
FIG. 1 is a stylized representation of a medical procedure in accordance with this detailed description.

FIG. 1 is a stylized representation of a medical procedure in accordance with this detailed description. In the procedure of FIG. 1, a physician is treating an eye 20 of a patient P. The physician is holding a hand piece of a delivery system 70 in his or her right hand RH. The physician's left hand LH is holding the handle H of a gonio lens 23 in the procedure of FIG. 1. Some physicians may prefer holding the delivery system hand piece in the right hand and the gonio lens handle in the left hand.

During the procedure illustrated in FIG. 1, the physician may view the interior of the anterior chamber using gonio lens 23 and a microscope 25. Detail A of FIG. 1 is a stylized simulation of the image viewed by the physician. A distal portion of a cannula 72 is visible in Detail A. A shadow-like line indicates the location of Schlemm's canal SC, which is a tube-like structure that encircling the iris and lying under various tissue (e.g., the trabecular meshwork) that surround the anterior chamber. A distal opening 74 of cannula 72 is positioned near Schlemm's canal SC of eye 20.

Methods in accordance with this detailed description may include the step of advancing the distal end of cannula 72 through the cornea of eye 20 so that a distal portion of cannula 72 is disposed in the anterior chamber of the eye. Cannula 72 may then be used to access Schlemm's canal of the eye, for example, by piercing the wall of Schlemm's canal with the distal end of cannula 72. Distal opening 74 of cannula 72 may be placed in fluid communication with a lumen defined by Schlemm's canal. An ocular implant carried by the cannula may be advanced out of distal opening 74 and into Schlemm's canal. Insertion of the ocular implant into Schlemm's canal may facilitate the flow of aqueous humor out of the anterior chamber of the eye. Examples of ocular implants that may be delivered through the cannula of this invention may be found, e.g., in U.S. Pat. Nos. 7,740,604; 8,267,882; 8,425,449; US Patent Publ. No. 2009/0082860 (now U.S. Pat. No. 8,734,377); and US Patent Publ. No. 2009/0082862.

Figure 2:
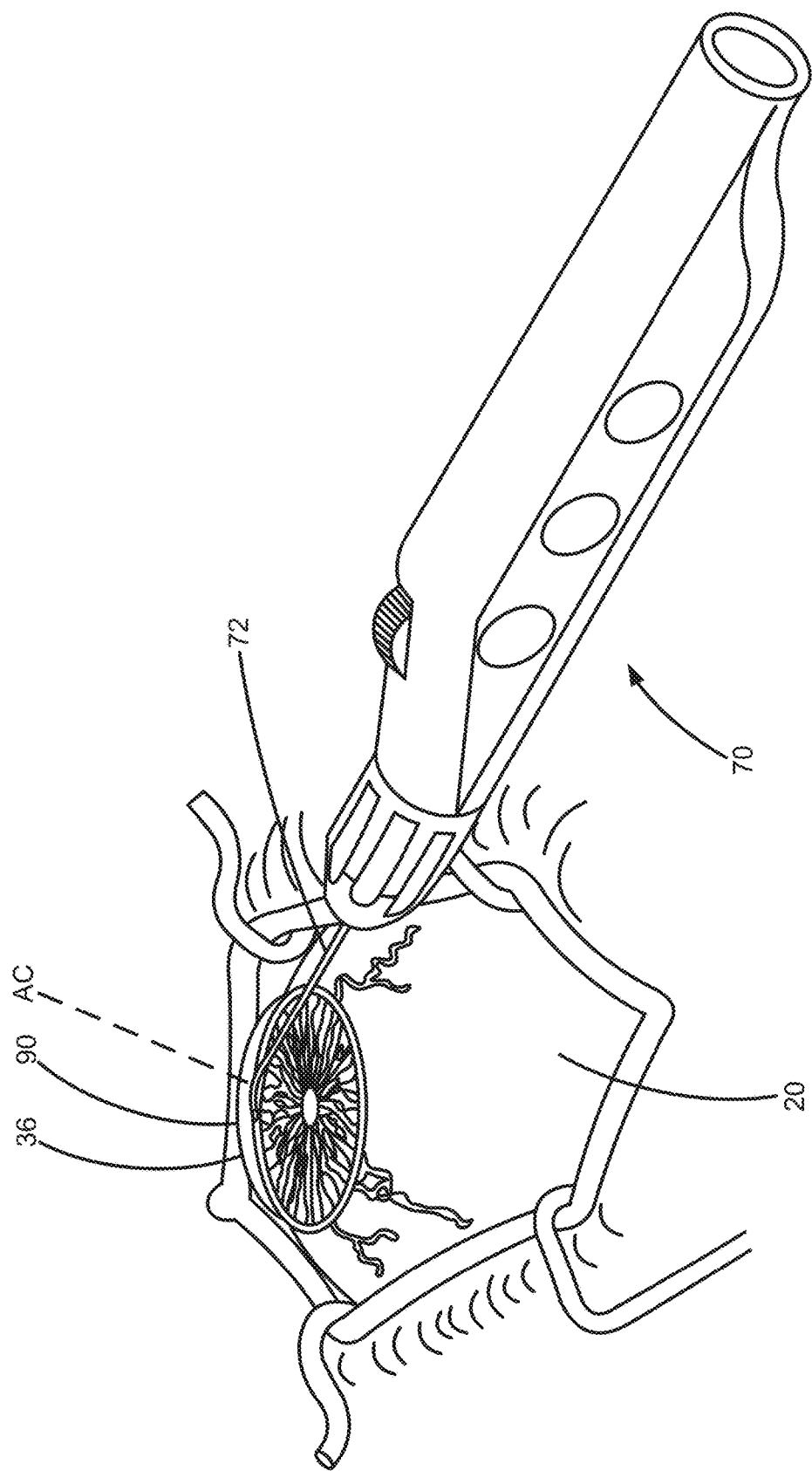
FIG. 2 is an enlarged perspective view further illustrating the delivery system and the eye shown in the previous figure.

FIG. 2 is an enlarged perspective view further illustrating delivery system 70 and eye 20 shown in the previous figure. In FIG. 2, cannula 72 of delivery system 70 is shown being advanced and extending through a dome-shaped wall 90 of eye 20. Dome shaped wall 90 includes the cornea 36 of eye 20 and scleral tissue that meets the cornea at a limbus of the eye. A distal portion of cannula 72 is disposed inside the anterior chamber AC defined by dome-shaped wall 90. In the embodiment of FIG. 2, cannula 72 is sized and configured so that a distal opening of cannula 72 can be placed in fluid communication with Schlemm's canal while a proximal portion of cannula 72 is extending through an incision in cornea 36.

In the embodiment of FIG. 2, an ocular implant (not shown) is disposed in a lumen or passageway within cannula 72. Delivery system 70 includes a mechanism that is capable of advancing and retracting the ocular implant along the length of cannula 72. Suitable delivery systems are described in more detail in, e.g., U.S. Pat. Nos. 8,512,404; 8,337,509; US Patent Publ. No. 2011/0009874 (now U.S. Pat. No. 9,693,899); and US Patent Publ. No. 2013/0158462 (now U.S. Pat. No. 8,663,150). The ocular implant may be placed in Schlemm's canal of eye 20 by advancing the ocular implant through the distal opening of cannula 72 while the distal opening is in fluid communication with Schlemm's canal.

Figure 3B:
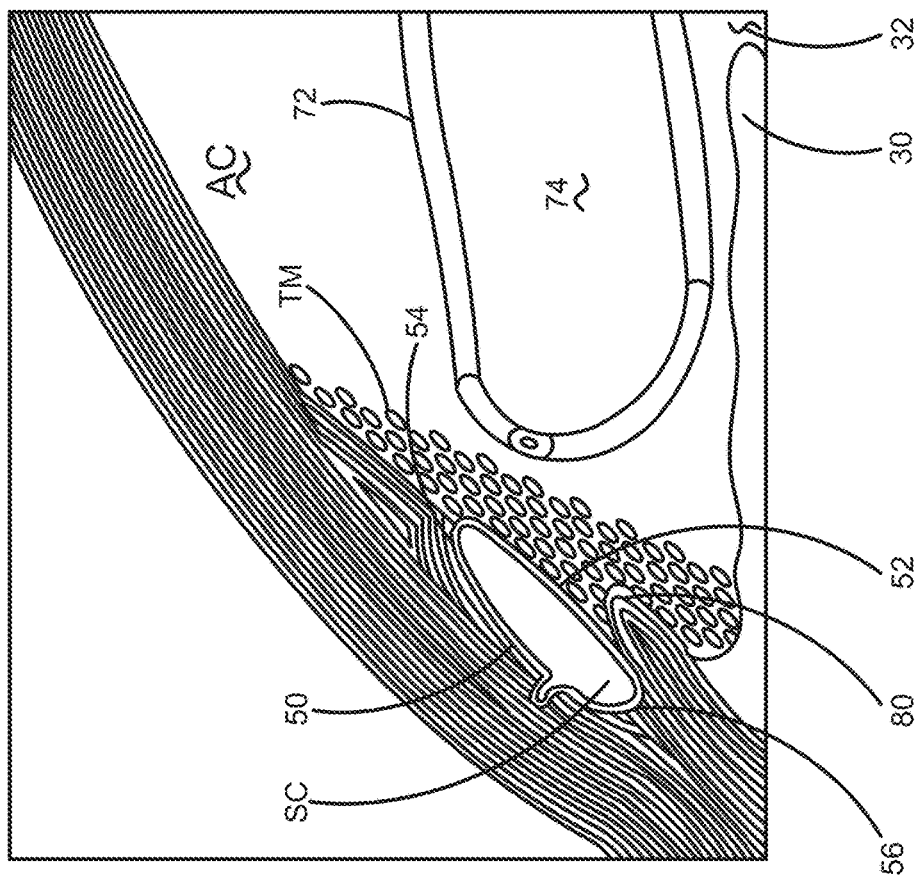
FIG. 3B is a section view further illustrating the eye shown in FIG. 3A.
Figure 3A:
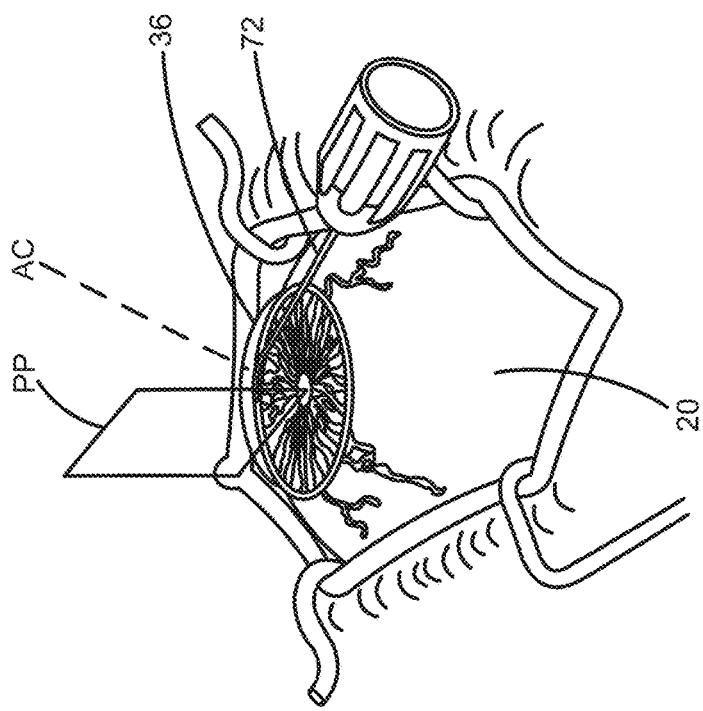
FIG. 3A is a perspective view further illustrating the eye and cannula shown in the previous figure.

FIG. 3A is a perspective view further illustrating eye 20 shown in the previous figure. In FIG. 3A, cannula 72 is shown extending through a cornea 36 of eye 20. In FIG. 3B, a distal opening 74 of cannula 72 is shown disposed inside an anterior chamber AC of eye 20. In FIG. 3A, a cutting plane PP is shown extending across eye 20. FIG. 3B is a stylized cross-sectional view taken along cutting plane PP shown in FIG. 3A. The cutting plane of FIG. 3A extends laterally across Schlemm's canal SC and the trabecular meshwork TM of the eye.

Eye 20 includes an iris 30 that defines a pupil 32 of the eye. Schlemm's canal SC forms a ring around iris 30 with pupil 32 disposed in the center of that ring. Schlemm's canal SC has a first major side 50, a second major side 52, a first minor side 54, and a second minor side 56. First major side 50 is on the outside of the ring formed by Schlemm's canal SC and second major side 52 is on the inside of the ring formed by Schlemm's canal SC. Accordingly, first major side 50 may be referred to as an outer major side of Schlemm's canal SC and second major side 52 may be referred to as an inner major side of Schlemm's canal SC. With particular reference to FIG. 3B, it will be appreciated that first major side 50 is further from pupil 32 than second major side 52. In the schematic view shown in FIG. 3A, first major side 50 is an outer major side of Schlemm's canal SC and second major side 52 is an inner major side of Schlemm's canal SC. A scleral spur 80 extends around minor side 56 toward the trabecular meshwork TM.

Figure 3C:
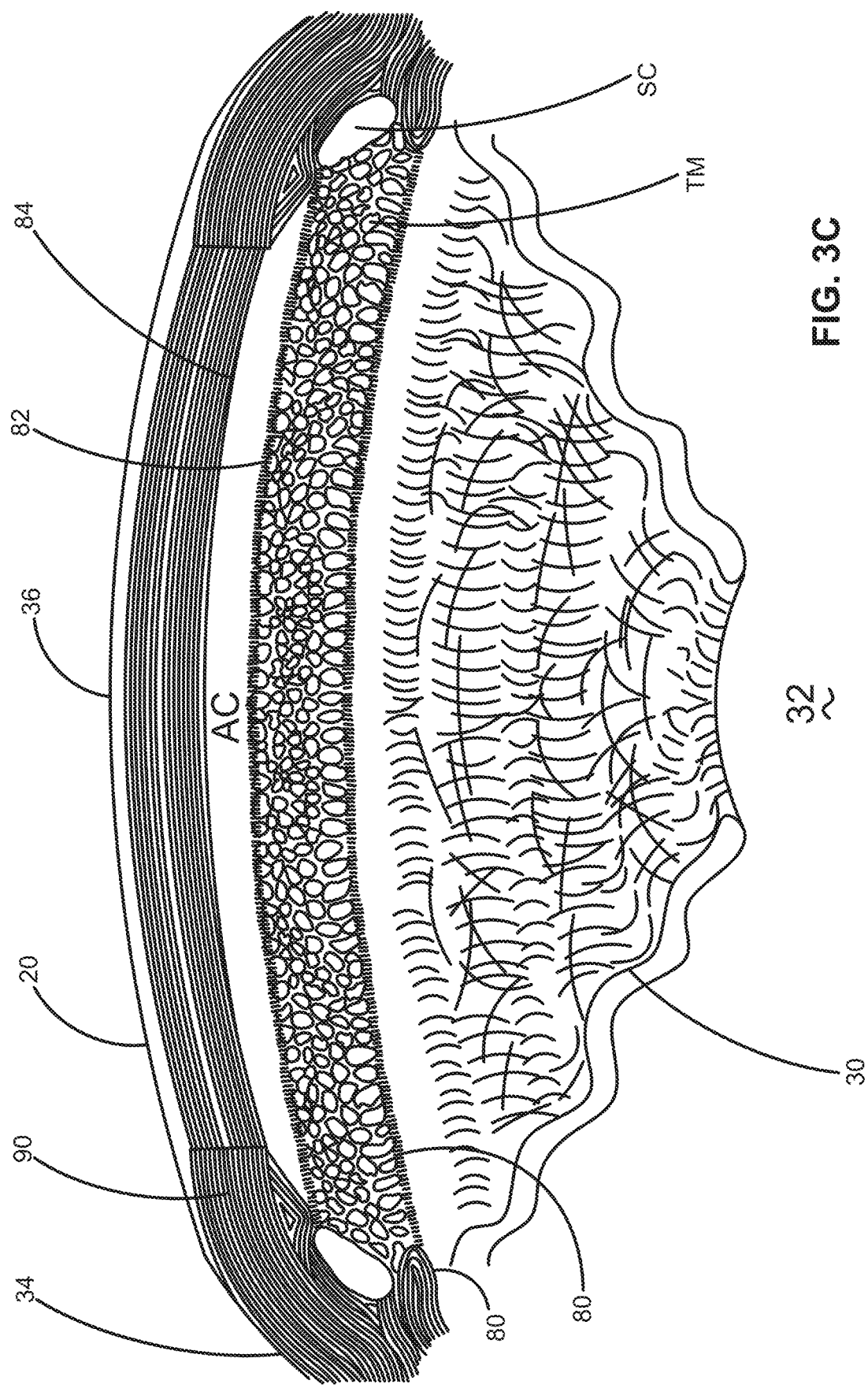
FIG. 3C is perspective view further illustrating the anatomy of the eye shown in FIG. 3B.

FIG. 3C is perspective view further illustrating the anatomy of eye 20 shown in FIG. 3B. Eye 20 includes a dome-shaped wall 90 that defines and encloses the anterior chamber AC. Dome-shaped wall 90 comprises a cornea 36 and scleral tissue 34. The scleral tissue 34 meets the cornea 36 at a limbus of eye 20. Dome-shaped wall 90 includes a scleral spur 80 that encircles anterior chamber AC. Schlemm's canal SC resides in a shallow depression in the scleral tissue located near scleral spur 80. The trabecular meshwork TM is fixed to scleral spur 80 and extends over Schlemm's canal. Together, Schlemm's canal SC, trabecular meshwork TM, and scleral spur 80 encircle anterior chamber AC along dome-shaped wall 90. Iris 30 of eye 20 is disposed inside the anterior chamber AC. Iris 30 defines a pupil 32. Schwalbe's line 82 is disposed at the end of Descemet's membrane 84. Descemet's membrane 84 is one of the inner-most layers of cornea 36. Descemet's membrane extends across cornea 36 toward Schlemm's canal SC and terminates near the upper edge of Schlemm's canal SC.

Figure 3D:
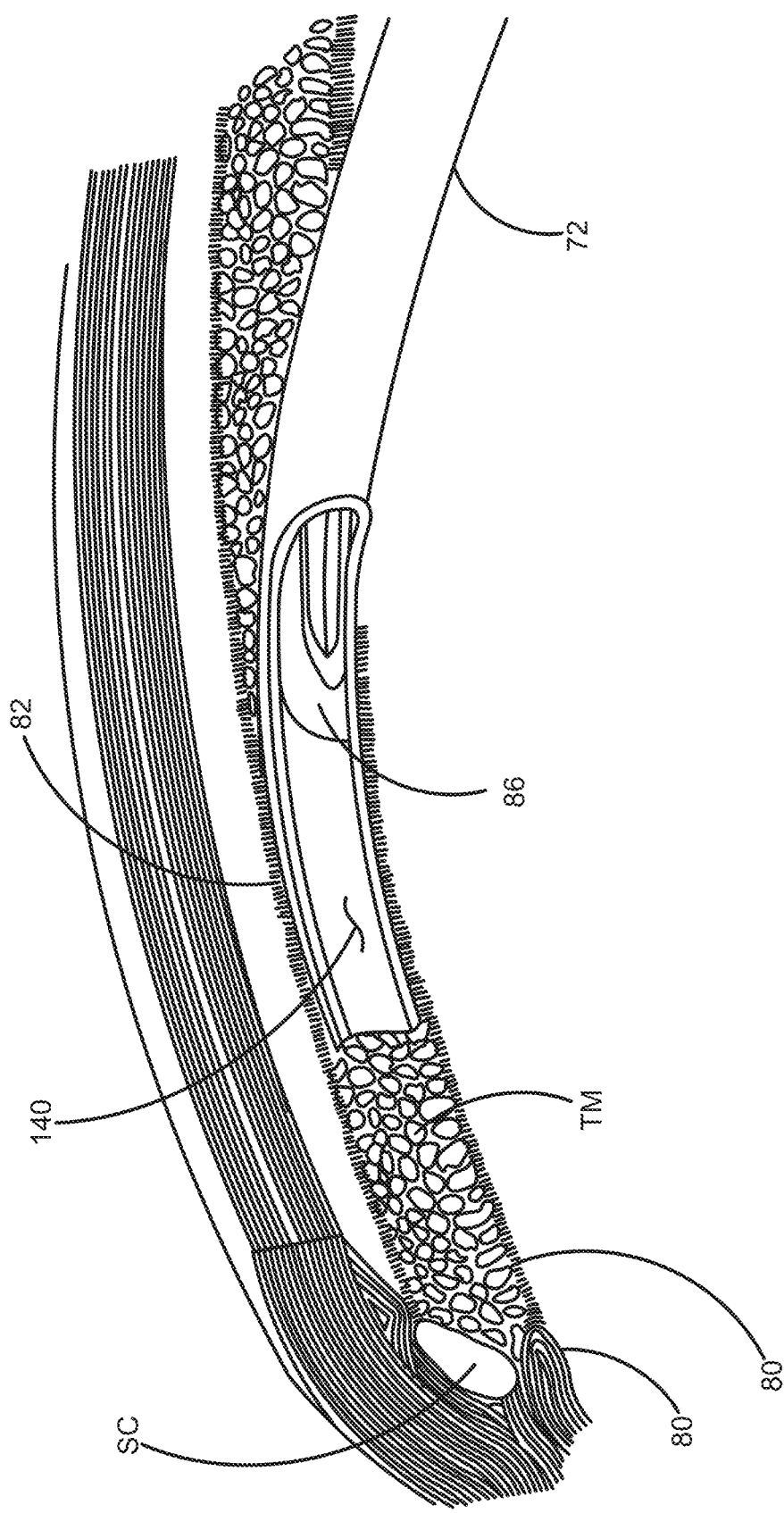
FIG. 3D is a perspective view showing a portion of eye shown in FIG. 3C.

FIG. 3D is a perspective view showing a portion of eye shown in the previous figure. In FIG. 3D, the tip portion of a cannula 72 can be seen extending into trabecular meshwork TM. In some useful embodiments, cannula 72 can be curved to achieve substantially tangential entry into Schlemm's canal SC. Also in the embodiment of FIG. 3D, a curved distal portion of cannula 72 is dimensioned to be disposed within the anterior chamber of the eye. In FIG. 3D, an ocular implant 86 can be seen extending from a lumen in cannula 72 into a trough 140 defined by cannula 72. Ocular implant 86 can be advanced through a distal opening of cannula 72 along the trough 140 and into Schlemm's canal SC. Scleral spur 80 and Schwalbe's line 82 are also visible in FIG. 3D.

Figure 3E:
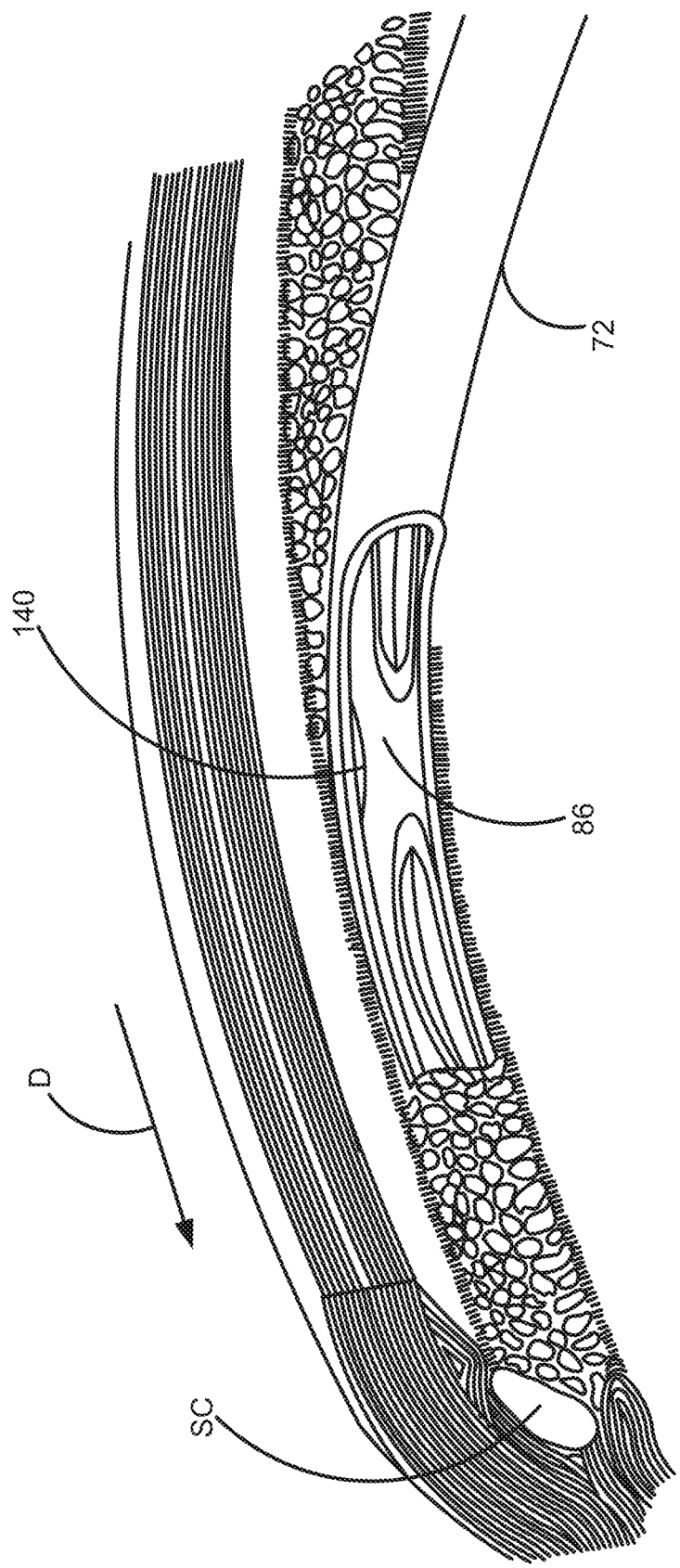
FIG. 3E is an additional perspective view showing the ocular implant and the cannula shown in FIG. 3D.

FIG. 3E is an additional perspective view showing ocular implant 86 and cannula 72 shown in the previous figure. By comparing FIG. 3E with the previous figure, it will be appreciated that ocular implant 86 has been advanced in a distal direction D while cannula 72 has remained stationary so the distal end of ocular implant 86 is disposed inside Schlemm's canal SC and the remainder of the implant is disposed in trough 140 and inside the lumen of the cannula. Trough 140 opens into an elongate opening extending through the side wall of cannula 72. In the embodiment of FIG. 3E, the elongate opening defined by the cannula provides direct visualization of the ocular implant as it is advanced into Schlemm's canal. A configuration allowing direct visualization of the ocular implant has a number of clinical advantages. During a medical procedure, it is often difficult to monitor the progress of the implant by viewing the implant through the trabecular meshwork. For example, blood reflux may push blood into Schlemm's canal obstructing a physician's view the portion of the implant that has entered Schlemm's canal. With reference to FIG. 3E, ocular implant 86 tracks along trough 140 as it is advanced distally along cannula 72 into Schlemm's canal. The trough opening allows the physician to monitor the progress of the implant by viewing the implant structures as they advance through the trough prior to entering Schlemm's canal. The trough opening also allows the physician to identify the position of the proximal end of the ocular implant with respect to the incision made by the cannula to access Schlemm's canal.

The ocular implants referenced above are intended to reside partially or wholly within Schlemm's canal. One function of the cannula is to deliver a leading edge of the ocular implant into Schlemm's canal so that the ocular implant can be advanced circumferentially into Schlemm's canal. The cannula of this invention provides features to help the user guide the distal end of the cannula into Schlemm's canal. These cannula features take advantage of the shapes and properties of the various tissue structures of and around Schlemm's canal to achieve this goal.

When inserting a cannula through the anterior chamber and the trabecular meshwork into Schlemm's canal under gonio lens visualization, the physician may use anatomical landmarks to guide the cannula placement and advancement. One convenient landmark is scleral spur 80 which has the appearance of a white line encircling the anterior chamber AC. Another convenient landmark is a pigment line centered on Schlemm's canal SC. An additional convenient landmark is Schwalbe's line 82.

Figure 4:
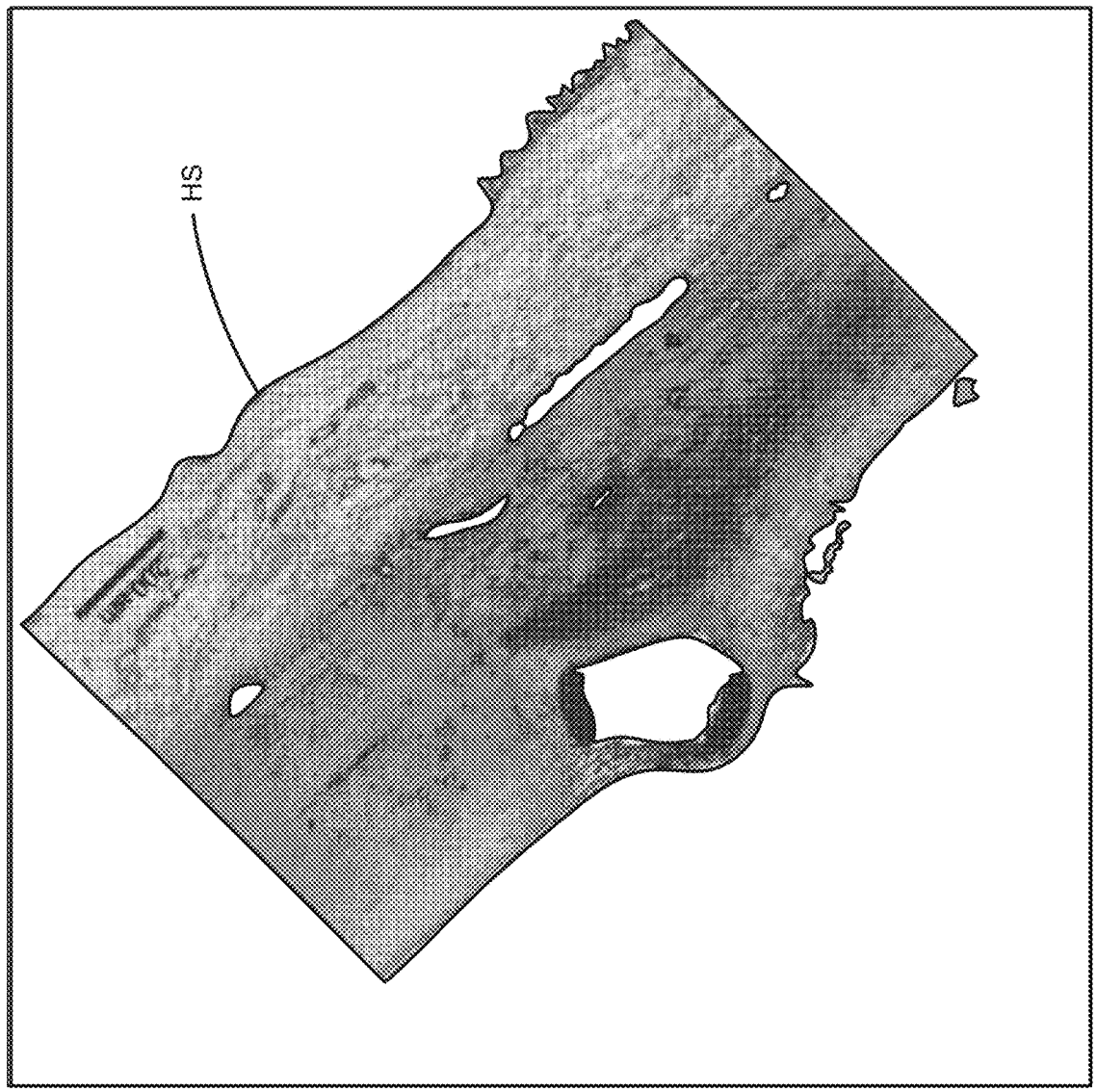
FIG. 4 is a photographic image showing a histology slide HS. Histology slide HS of FIG. 4 was created by sectioning and staining tissue from a cadaveric eye. An ocular implant was implanted in Schlemm's canal of the cadaveric eye prior to sectioning.

An ocular implant residing in Schlemm's canal of a cadaveric eye can be seen in FIG. 4. FIG. 4 is a photographic image showing a histology slide HS. Histology slide HS of FIG. 4 was created by implanting the ocular implant into Schlemm's canal of the eye, then sectioning and staining a portion of the eye. The photograph of FIG. 4 was created while examining the section of tissue using a light microscope.

Figures 5A, 5B:
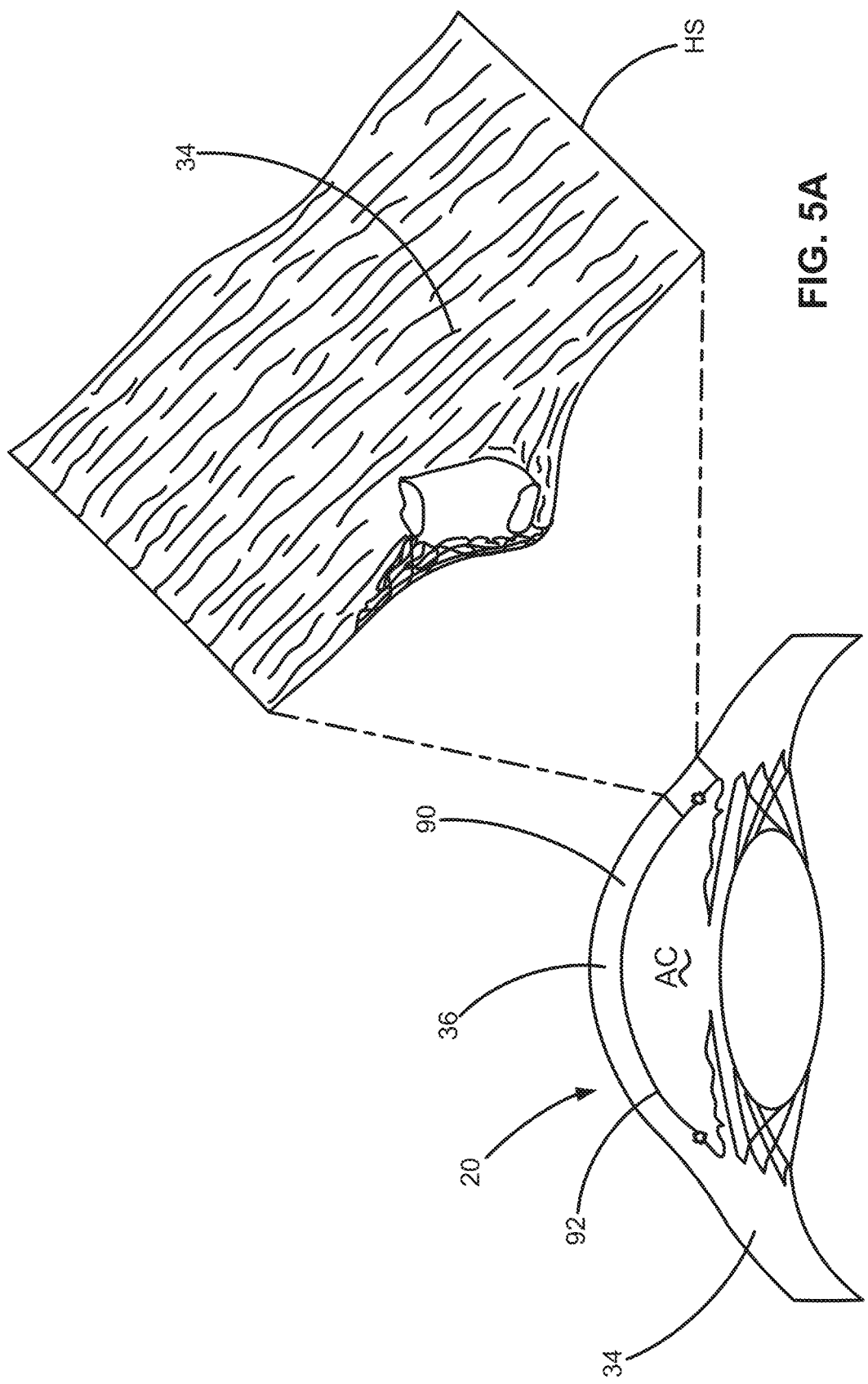
FIG. 5A is a stylized line drawing illustrating histology slide HS shown in the previous figure.
FIG. 5B is a simplified cross-sectional view illustrating the eye from which the histology sample was taken.

FIG. 5A is a stylized line drawing illustrating histology slide HS shown in the previous figure. FIG. 5B is a simplified cross-sectional view illustrating the eye from which the histology sample was taken. FIG. 5A and FIG. 5B are presented on a single page to illustrate the location of the histology sample relative to other portions of the eye 20. Eye 20 includes a dome-shaped wall 90 having a surface 92 defining an anterior chamber AC. Dome-shaped wall 90 of eye 20 comprises a cornea 36 and scleral tissue 34. The scleral tissue 34 meets the cornea 36 at a limbus of the eye. In FIG. 5B, surface 92 is shown having a generally hemispherical shape.

Figure 6:
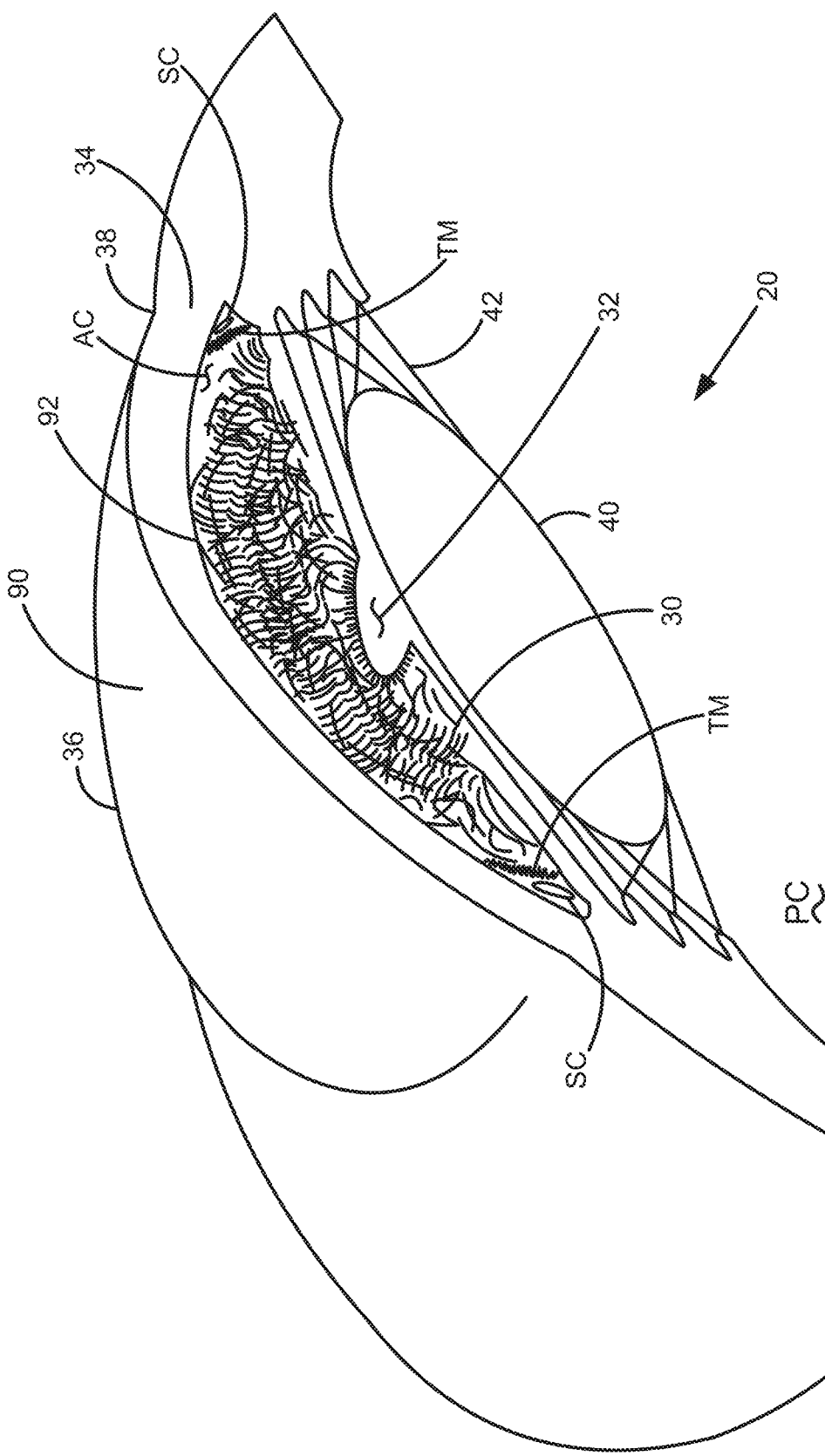
FIG. 6 is a stylized perspective view illustrating the anatomy of an eye.

FIG. 6 is a stylized perspective view illustrating a portion of eye 20 discussed above. Eye 20 includes an iris 30 defining a pupil 32. In FIG. 6, eye 20 is illustrated in a cross-sectional view created by a cutting plane passing through the center of pupil 32. Eye 20 includes a dome-shaped wall 90 having a surface 92 defining an anterior chamber AC. In FIG. 6, surface 92 is shown having a generally hemispherical shape. Dome-shaped wall 90 of eye 20 comprises a cornea 36 and scleral tissue 34. The scleral tissue 34 meets the cornea 36 at a limbus 38 of eye 20. Additional scleral tissue 34 of eye 20 surrounds a posterior chamber PC filled with a viscous fluid known as vitreous humor. A lens 40 of eye 20 is located between anterior chamber AC and posterior chamber PC. Lens 40 is held in place by a number of ciliary zonules 42.

Whenever a person views an object, he or she is viewing that object through the cornea, the aqueous humor, and the lens of the eye. In order to be transparent, the cornea and the lens can include no blood vessels. Accordingly, no blood flows through the cornea and the lens to provide nutrition to these tissues and to remove wastes from these tissues. Instead, these functions are performed by the aqueous humor. A continuous flow of aqueous humor through the eye provides nutrition to portions of the eye (e.g., the cornea and the lens) that have no blood vessels. This flow of aqueous humor also removes waste from these tissues.

Aqueous humor is produced by an organ known as the ciliary body. The ciliary body includes epithelial cells that continuously secrete aqueous humor. In a healthy eye, a stream of aqueous humor flows out of the eye as new aqueous humor is secreted by the epithelial cells of the ciliary body. This excess aqueous humor enters the blood stream and is carried away by venous blood leaving the eye.

In the illustration of FIG. 6, the cutting plane passing through the center of pupil 32 has also passed through Schlemm's canal. Accordingly, two laterally cut ends of Schlemm's canal SC are visible in the cross-sectional view of FIG. 6. In a healthy eye, aqueous humor flows out of anterior chamber AC and into Schlemm's canal SC. Aqueous humor exits Schlemm's canal SC and flows into a number of collector channels. After leaving Schlemm's canal SC, aqueous humor is absorbed into the venous blood stream and carried out of the eye.

Figure 7:
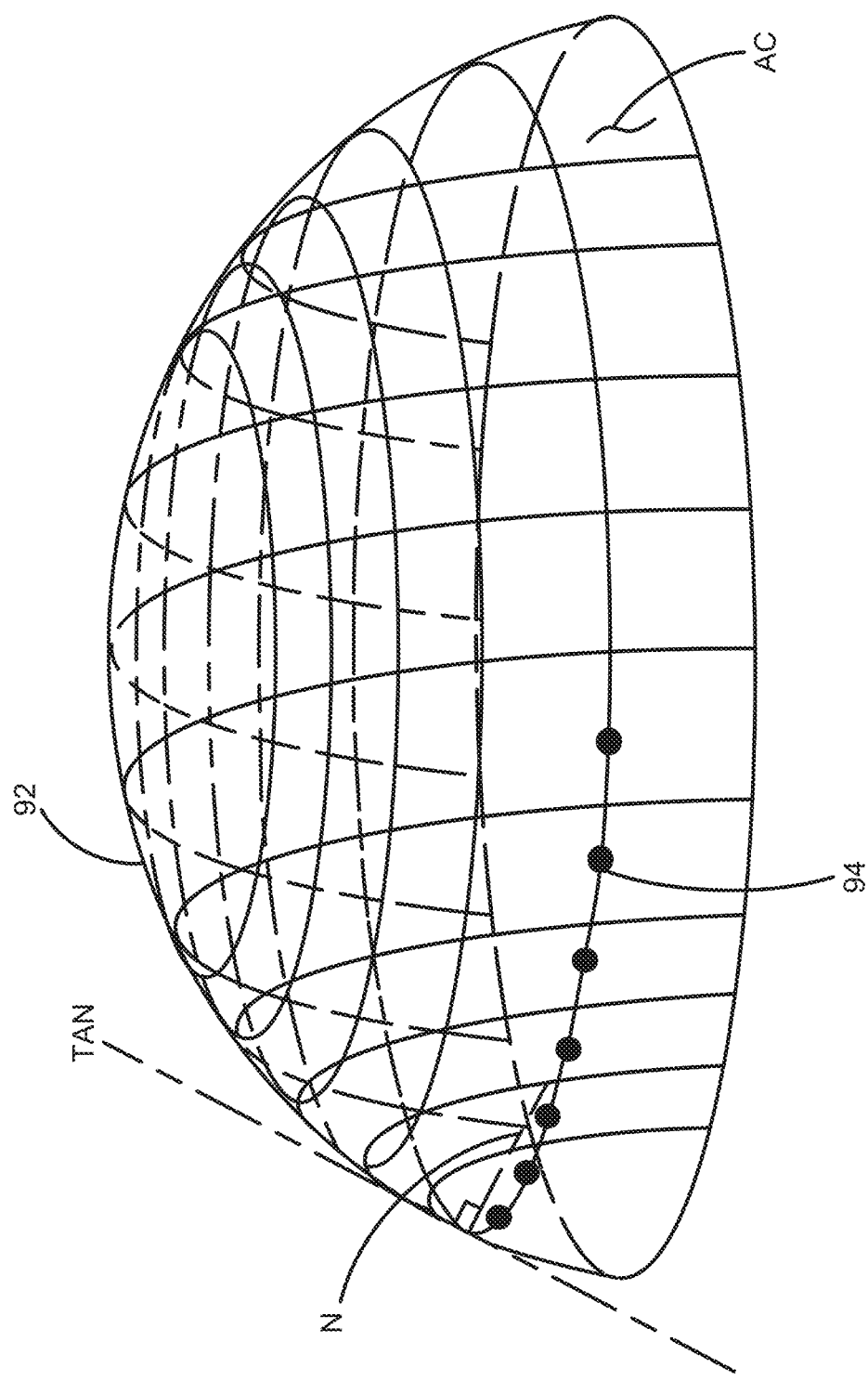
FIG. 7 is a stylized perspective view depicting the surface that defines the anterior chamber of the eye shown in FIG. 6.

FIG. 7 is a stylized perspective view depicting the surface 92 that defines anterior chamber AC of the eye shown in FIG. 6. In FIG. 7, surface 92 is shown having a generally hemispherical shape. FIG. 7 may be used to illustrate some fundamental geometric concepts that will be used below to describe the various ocular implant delivery cannula structures. Geometry is a branch of mathematics concerned with the properties of space and the shape, size, and relative position of objects within that space. In geometry, a sphere is a round object in three-dimensional space. All points on the surface of a sphere are located the same distance r from a center point so that the sphere is completely symmetrical about the center point. In geometry, a point represents an exact location. A point is a zero-dimensional entity (i.e., it has no length, area, or volume). Geometrically speaking, at any point on a spherical surface, one can find a normal direction which is at right angles to the surface. For a spherical surface all normal directions intersect the center point of the sphere. Each normal direction will also be perpendicular to a line that is tangent to the spherical surface. In FIG. 7, a normal line N is illustrated using dashed lines. Normal line N is at right angles to spherical surface 92. Normal line N is also perpendicular to a reference line TAN. Reference line TAN is tangent to spherical surface 92 in FIG. 7.

A method in accordance with this detailed description may include the step of advancing a distal portion of a cannula into the anterior chamber of the eye. The cannula may then be used to access Schlemm's canal, for example, by piercing the wall of Schlemm's canal with the distal end of the cannula. An ocular implant may be advanced out of the distal opening of the cannula and into Schlemm's canal. A path 94 taken by an ocular implant as it follows Schlemm's canal along surface 92 is illustrated using a row of dots in FIG. 7.

Scleral tissue above the trabecular meshwork, and the scleral spur below the trabecular meshwork, are harder than the meshwork tissue. If the physician advances the cannula's distal tip against the scleral tissue above the canal, the angle of the scleral tissue with respect to the approach angle of the cannula, as well as the hardness of that tissue, will tend to guide the cannula tip downward toward and into the meshwork. This effect can be enhanced if the cannula's distal tip is sharp enough to easily penetrate the meshwork but not sharp enough to easily pierce scleral tissue. If, on the other hand, the physician advances the cannula's distal tip onto the scleral spur below the meshwork, the cannula is likely to miss the meshwork and Schlemm's canal altogether.

Likewise, as the ocular implant advances into Schlemm's canal, the ocular implant may press against the scleral tissue supporting the outer major wall of Schlemm's canal and the scleral tissue of the dome-shaped wall that defines the anterior chamber of the eye. As the body of the ocular implant presses against the dome-shaped wall of the eye, the dome-shaped wall provides support for Schlemm's canal and the ocular implant. The support provided by the dome-shaped wall may be represented by force vectors. The direction of these force vectors may be at right angles to points on the spherical surface that defines the anterior chamber. Accordingly, the outer major wall of Schlemm's canal may be supported by the dome shaped wall as the ocular implant advances circumferentially into Schlemm's canal.

During delivery, it is desirable that the ocular implant follow the lumen of Schlemm's canal as it is advanced out the distal opening of the cannula. The ability of the ocular implant to be advanced into and follow the lumen of Schlemm's canal may be referred to as trackability. Characteristics of an ocular implant that effect trackability include axial pushability and lateral flexibility. Axial pushability generally concerns the ability of an ocular implant to transmit to the distal end of the ocular implant an axial force applied to the proximal end of the ocular implant. Lateral flexibility concerns the ease with which the ocular implant body can bend to conform to the shape of the lumen. Trackability may be adversely affected when twisting forces are applied to a curved body. For example, twisting the body of a curved ocular implant about its longitudinal axis may cause the curved body to steer away from a desired path.

Figure 8:
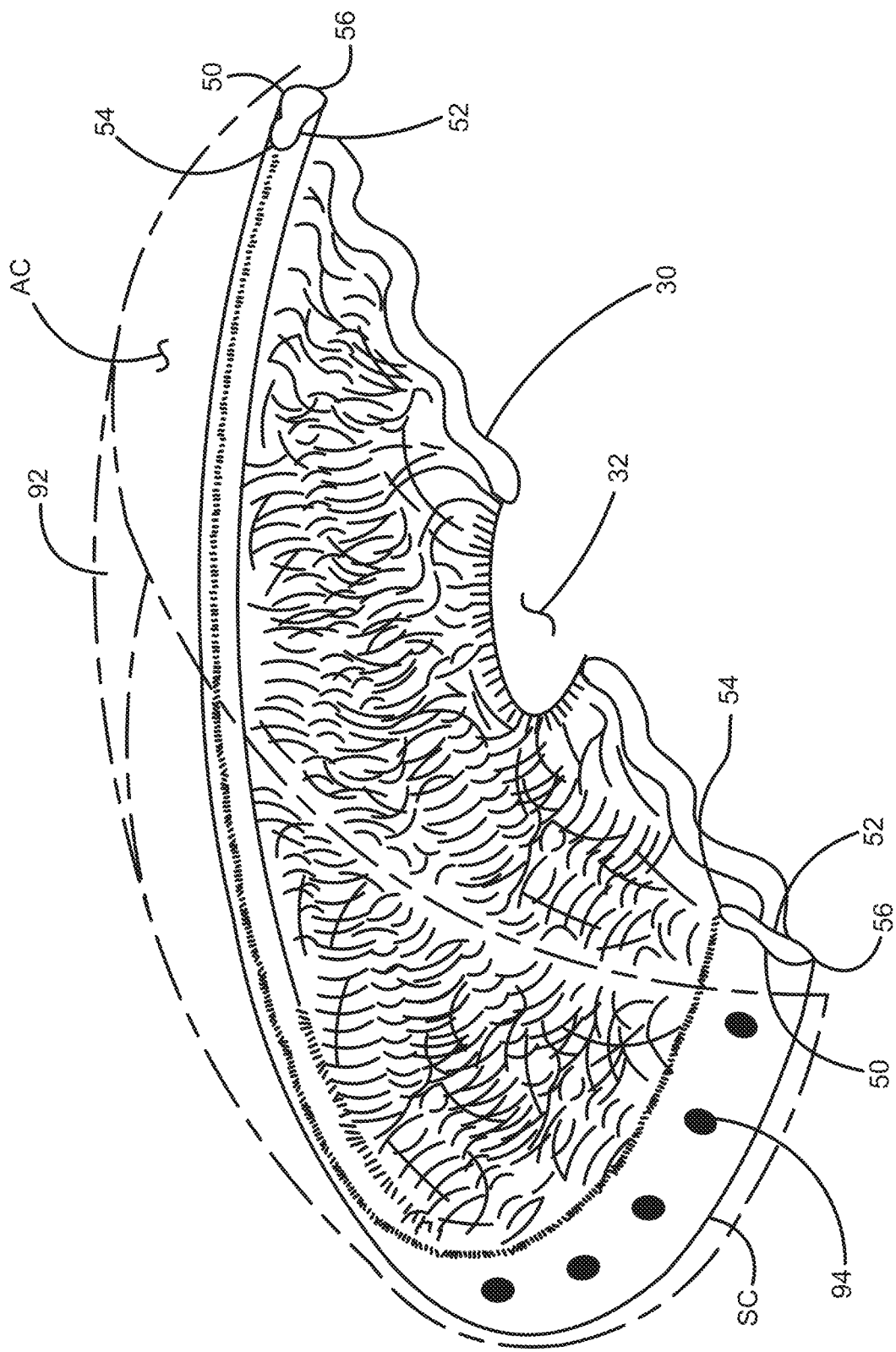
FIG. 8 is a stylized perspective view further illustrating Schlemm's canal SC and iris 30 shown in FIG. 6.

FIG. 8 is a stylized perspective view further illustrating Schlemm's canal SC and iris 30 shown in FIG. 6. The surface 92 that defines the anterior chamber AC of eye 20 is depicted using dashed lines in FIG. 8. In the embodiment of FIG. 8, Schlemm's canal SC and iris 30 are shown in cross-section, with a cutting plane passing through the center of a pupil 32 defined by iris 30. Schlemm's canal SC comprises a first major side 50, a second major side 52, a first minor side 54, and a second minor side 56. Schlemm's canal SC forms a ring around iris 30 with pupil 32 disposed in the center of that ring. With reference to FIG. 8, it will be appreciated that first major side 50 is on the outside of the ring formed by Schlemm's canal SC and second major side 52 is on the inside of the ring formed by Schlemm's canal SC. Accordingly, first major side 50 may be referred to as an outer major side of Schlemm's canal SC and second major side 52 may be referred to as an inner major side of Schlemm's canal SC. With reference to FIG. 8, it will be appreciated that first major side 50 is further from pupil 32 than second major side 52.

A path 94 taken by an ocular implant as it follows Schlemm's canal along surface 92 is illustrated using a row of dots in FIG. 8. As the ocular implant advances into Schlemm's canal, the ocular implant may press against the outer major wall of Schlemm's canal and the dome-shaped wall that defines the anterior chamber.

Some embodiments include an ocular implant delivery cannula with a distal tip that is offset from the longitudinal center line of the cannula. This arrangement facilitates the intuitive use of anatomical landmarks that can be easy observed using gonioscopic visualization. When the body of the cannula is generally centered on Schlemm's canal, the tip portion of the cannula will pierce the trabecular meshwork and the wall of Schlemm's canal at a point slightly above the center of Schlemm's canal. The offset distal tip also provides the distal end of the cannula with a lower camming surface for guiding the cannula distal end over the scleral spur and an optional upper camming surface for guiding the cannula distal end into Schlemm's canal when the cannula has a diameter larger than a width of Schlemm's canal. The camming surfaces are configured to direct the cannula into Schlemm's canal when the cannula is wider or oversized with respect to a width of the canal.

Figure 9C:
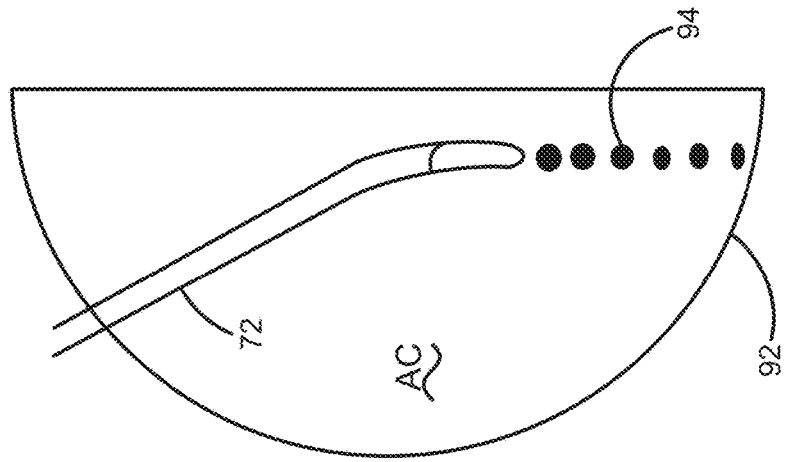
FIGS. 9A-9C are plan views of the surface that defines anterior chamber of the eye shown in FIG. 6.
Figure 9B:
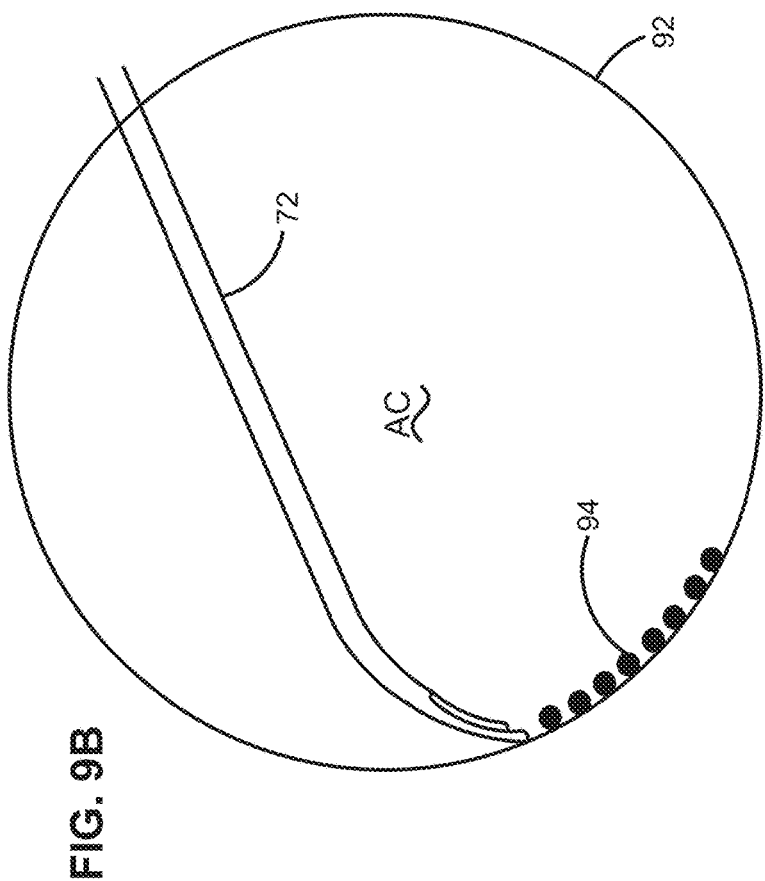
Figure 9A:
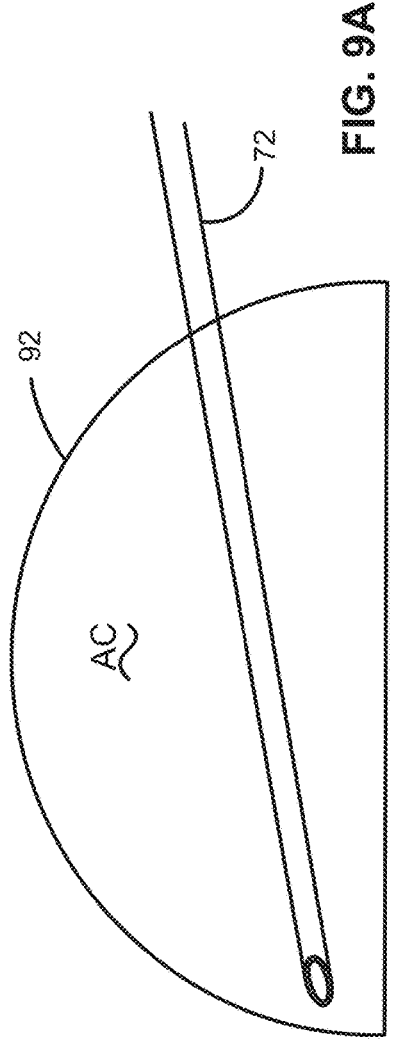

FIGS. 9A-9C are plan views of the surface 92 that defines anterior chamber AC of the eye shown in FIG. 6. FIG. 9A may be referred to as a front view of surface 92, FIG. 9B may be referred to as a top view of surface 92, and FIG. 9C may be referred to as a side view of surface 92.

In FIGS. 9A-9C, a cannula 72 is shown extending into anterior chamber AC. Cannula 72 may be used to deliver an ocular implant to a target location within anterior chamber AC. Examples of target locations that may be suitable in some applications include areas in and around Schlemm's canal, the trabecular meshwork, and the suprachoroidal space of an eye. A path 94 that may be taken by an ocular implant as it follows Schlemm's canal along surface 92 is illustrated using a row of dots in FIGS. 9A-9C.

Figure 10:
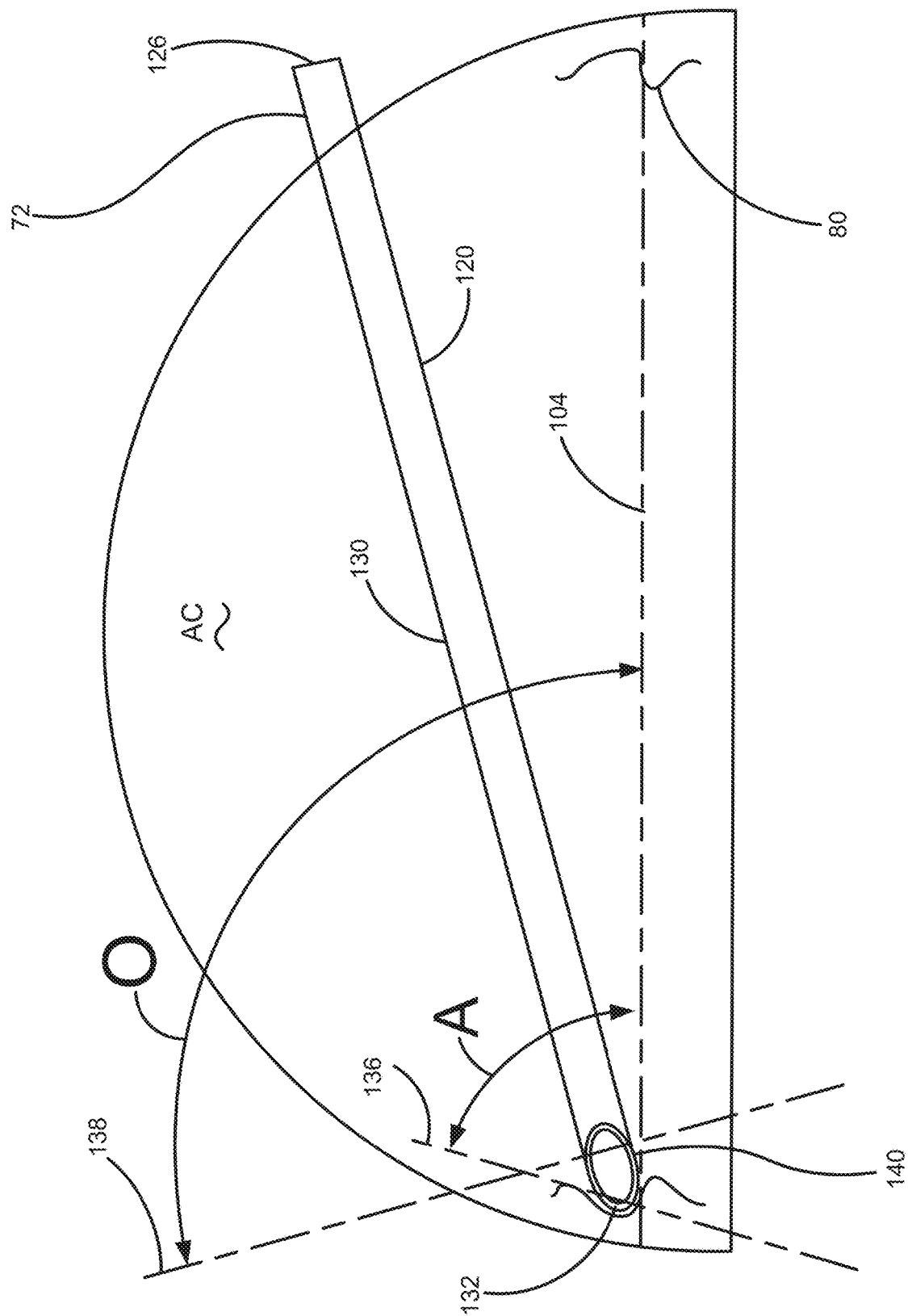
FIG. 10 is an enlarged side view showing a cannula extending into anterior chamber defined by an inner surface of a dome shaped wall.

FIG. 10 is an enlarged side view showing cannula 72 extending into anterior chamber AC defined by surface 92. Cannula 72 may be used, for example, to deliver an ocular implant to a target location within Schlemm canal SC. In the stylized plan view of FIG. 10, a scleral spur 80 is disposed in anterior chamber AC. Scleral spur 80 is fixed to surface 92 and encircles anterior chamber AC. Scleral spur 80 defines a spur plane 104.

Referring still to FIG. 10, cannula 72 can include a body member 120 extending along a longitudinal axis. Body member 120 can include a proximal end 126 and a tubular portion 130 extending distally from the proximal end. Body member 120 can also include a tip portion 132 disposed at a distal end thereof. A trough portion 140 of body member extends between tip portion 132 and tubular portion 130. In the embodiment of FIG. 10, tip portion 132 has a semi-circular transverse cross-section including a tip chord line segment. A secant 136 extending beyond the tip chord is shown in FIG. 10. Trough portion 140 of body member 120 has a semi-circular transverse cross-section including a trough chord line segment. FIG. 10 includes a secant 138 extending beyond the trough cord.

As shown in FIG. 10, tip portion 132 and trough portion 140 are adapted and configured such that, when tubular portion 130 is extending through an incision in the dome shaped wall defining anterior chamber AC and tip portion 132 is extending into Schlemm's canal of the eye, secant 136 intersects spur plane 104 at an acute angle A and secant 138 intersects spur plane 104 at an obtuse angle 0.

FIGS. 11A-11C are plan views of cannula 72 created using multiview projection. FIG. 11D is an axial view further illustrating cannula 72. Cannula 72 of FIGS. 1A-11D may be used to deliver an ocular implant into Schlemm's canal of an eye. FIG. 11A may be referred to as a top view of cannula 72, FIG. 11B may be referred to as a side view of cannula 72, and FIG. 11C may be referred to as a bottom view of cannula 72.

In FIGS. 11A-11D, cannula 72 comprises a body member 120 extending along a medial plane 122. Body member 120 can include a proximal end 126 and a tubular portion extending distally from the proximal end. Body member 120 can also include a tip portion 132 disposed at a distal tip 128 thereof. The distal tip 128 can be offset from the medial plane 122 of body member 120. The distal tip 128 can form a point at the intersection of lower camming surface 129 and upper camming surface 131. In one alternative embodiment, the distal tip may be at one side of the cannula, in which case there will be no upper camming surface. In some embodiments, distal tip 128 can be sharpened enough to pierce trabecular meshwork tissue but not sharp enough to easily pierce scleral tissue.

Body member 120 also includes a trough portion 140 extending between distal tip 128 and tubular portion 130. Trough portion 140 is configured to fluidly communicates with a lumen 144 defined by tubular portion 130 and a distal opening 142 defined by tip portion 132. Because of the offset position of distal tip 128, tip portion 132 is asymmetric about medial plane 122 and trough portion 140 is symmetric about medial plane 124.

FIG. 12A through FIG. 12D are lateral cross-sectional views of tip portion 132 of cannula 72. FIG. 12E is a lateral cross-sectional view of trough portion 140 of cannula 72. FIG. 12F is an enlarged plan view showing a portion of cannula 72 shown in the previous figure. In this embodiment, the cannula is formed from a tube (such as a hypotube) with material removed from the distal end to form the trough portion and the distal tip 129. In other embodiments, the cannula may have a non-tubular shape. FIG. 12F shows the cannula 72 including the tip portion 132, distal tip 128, camming surfaces 129 and 131, and trough portion 140. In FIG. 12F, a number of section lines can be seen traversing crossing cannula 72. These section lines have been used to create a number of lateral cross-sections illustrating the shape of cannula 72.

Section 146A of FIG. 12A was created by cutting tip portion 132 along section line A-A shown in FIG. 12F. Section 146B, section 146C, and section 146D, of FIGS. 12B, 12C, and 12D, respectively, were made by cutting tip portion 132 along section line B-B, section line C-C, and section line D-D, respectively. By examining section 146A, section 146B, section 146C and section 146D it will be appreciated that tip portion 132 can have a semi-circular transverse cross-section.

As shown in FIGS. 12A-12D, section 146A has a chord 136A. Section 146B, section 146C, and section 146D have a chord 136B, a chord 136C and a chord 136D, respectively. By examining chord 136A, chord 136B, chord 136C and chord 136D it will be appreciated that the chord length of tip portion 132 increases as tip portion 132 extends proximally away from its distal point. Section 146E was created by cutting through portion 140 along section line E-E shown in FIG. 12F. In the embodiment of FIG. 12E, section 146E has a chord 136E.

Referring to FIGS. 11A-11D and 12A-12E, as the physician advances the cannula through the anterior chamber toward the trabecular meshwork under visual guidance (using, e.g., the scleral spur, pigmented area and Schwalbe's line as anatomical landmarks), the camming surfaces 129 and 131 and the cannula's tip portion 132 are configured to guide an oversized cannula relative to the width of Schlemm's canal into Schlemm's canal. In some embodiments, a diameter of the cannula can be between approximately 350-550 microns, or alternatively, between 400-500 microns. Schlemm's canal typically has a width of approximately 300 microns, so it can be a challenge to guide a conventional cannula that is wider than Schlemm's canal into the canal. In the present embodiment, the upper camming surface 131 of the cannula will engage scleral tissue above the meshwork. Since the distal tip 128 is not sharp enough to easily pierce scleral tissue, upper camming surface 131 is configured to contact the scleral tissue and guide the distal tip 128 into Schlemm's canal. The lower camming surface 129 is configured to contact the scleral spur below the meshwork to guide the tip 128 into the Schlemm's canal. The distal tip's offset, placing it above the cannula's longitudinal center axis, along with the physician's use of the anatomical landmarks, helps ensure that the cannula is not positioned so low with respect to the meshwork that the upper camming surface engages the scleral spur to push the cannula tip downward away from the meshwork.

FIGS. 13A-13D form a sequence of stylized section views illustrating the insertion of tip portion 132 of cannula 72 into Schlemm's canal SC located in the anterior chamber AC of an eye. FIGS. 13E-13H form a sequence stylized side plan views further illustrating the insertion of the tip portion into Schlemm's canal.

In FIG. 13A and FIG. 13E, tip portion 132 of cannula 72 has been advanced into Schlemm's canal so that section 146A (shown in FIG. 12A) of tip portion 132 is aligned with the incision in Schlemm's canal created by the cannula's distal tip 128. Section 146A includes a chord 136A. Referring to FIG. 13A, chord 136A defines a line that intersects a spur plane 104 of the eye at a chord angle 148A. Spur plane 104 is defined by a scleral spur 102 that encircles the anterior chamber AC of the eye.

In FIG. 13B and FIG. 13F, tip portion 132 of cannula 72 has been advanced into Schlemm's canal so that section 146B of tip portion 132 is aligned with the incision in Schlemm's canal. Section 146B includes a chord 136B. In FIG. 13B, chord 136B defines a line that intersects spur plane 104 at a chord angle 148B.

In FIG. 13C and FIG. 13G, tip portion 132 of cannula 72 has been advanced into Schlemm's canal so that section 146C of tip portion 132 is aligned with the incision in Schlemm's canal. Section 146C includes a chord 136C. In FIG. 13C, chord 136C defines a line that intersects spur plane 104 at a chord angle 148C.

In FIG. 13D and FIG. 13H, tip portion 132 of cannula 72 has been advanced into Schlemm's canal so that section 146D of tip portion 132 is aligned with the incision in Schlemm's canal. Section 146D includes a chord 136D. In the embodiment of FIG. 13D, chord 136D defines a line that intersects spur plane 104 at a chord angle 148D.

Figure 14:
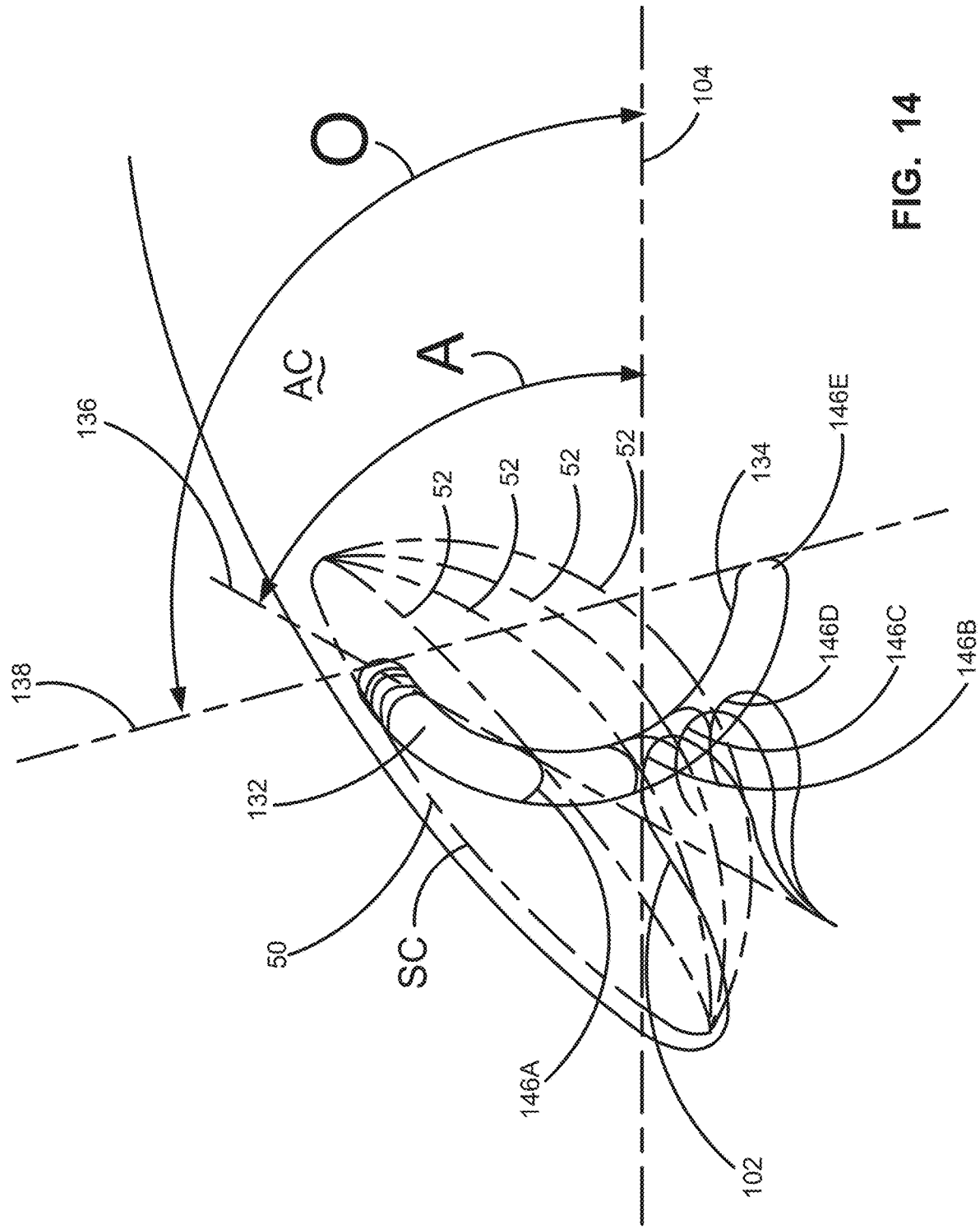
FIG. 14 is an abstract graphical representation further illustrating the insertion of the tip portion of a cannula into Schlemm's canal.

FIG. 14 is an abstract graphical representation further illustrating the insertion of tip portion 132 of a cannula into Schlemm's canal SC. The profile of each section view illustrated in FIGS. 12A-12D is included in FIG. 14. These profiles form contour lines illustrating the tapered shape of tip portion 132 and trough portion 140. The profiles associated with section 146A, section 146B, section 146C, section 146D, and section 146E are labeled in FIG. 14.

As tip portion 132 is inserted into Schlemm's canal, inner major wall 52 of Schlemm's canal rides along a first leading edge of tip portion 132. The insertion of tip portion 132 into Schlemm's canal SC causes inner major wall 52 to separate from outer major wall 50. The changing shape of Schlemm's canal is illustrated with a plurality of Schlemm's canal profiles shown using dashed lines in FIG. 14.

In the embodiment of FIG. 14, tip portion 132 and trough portion 140 are adapted and configured such that, when tubular portion 130 is extending through an incision in the dome shaped wall defining anterior chamber AC and tip portion 132 is extending into Schlemm's canal of the eye, secant 136 intersects spur plane 104 at an acute angle A and secant 138 intersects spur plane 104 at an obtuse angle θ.

While embodiments of the present invention have been shown and described, modifications may be made, and it is therefore intended in the appended claims to cover all such changes and modifications which fall within the true spirit and scope of the invention.

What is claimed is:

1. A cannula for delivering an ocular implant into Schlemm's canal of an eye, comprising:
a curved tube comprising a lumen configured to direct the ocular implant to a location within Schlemm's canal;
a trough portion disposed distally of the curved tube; and
a distal portion disposed distally of the trough portion, wherein the distal portion is asymmetric with respect to a medial plane of the curved tube, wherein the distal portion comprises a distal tip formed by an intersection of an upper camming surface and a lower camming surface, and wherein the distal tip is blunt.

2. The cannula of claim 1, wherein the distal portion is asymmetric with respect to the medial plane of the curved tube due to the upper camming surface being shorter than the lower camming surface.

3. The cannula of claim 1, wherein the lower camming surface is configured to guide the cannula over a scleral spur of the eye.

4. The cannula of claim 1, wherein the distal portion is defined by an asymmetric V-shape.

5. The cannula of claim 1, wherein the trough portion is symmetric with respect to the medial plane.

6. The cannula of claim 1, where the cannula is shaped and dimensioned so that at least part some of the trough portion is advanced into Schlemm's canal while a first portion of the curved tube is disposed inside an anterior chamber of the eye and a second portion of the curved tube is extended through an incision in the eye to a location outside of the eye.

7. An *ophthalmic* system, comprising:
a cannula comprising:
a curved tube comprising a lumen,
a trough portion disposed distally of the curved tube, and
a distal portion disposed distally of the trough portion, wherein the distal portion is asymmetric with respect to a medial plane of the curved tube, wherein the distal portion comprises a distal tip formed by an intersection of an upper camming surface and a lower camming surface, and wherein the distal tip is blunt; and
an ocular implant configured to be advanced distally through the lumen and along the trough portion into Schlemm's canal of an eye.

8. The system of claim 7, wherein the distal portion is asymmetric with respect to the medial plane of the curved tube due to the upper camming surface being shorter than the lower camming surface.

9. The system of claim 7, wherein the lower camming surface is configured to guide the cannula over a scleral spur of the eye.

10. The system of claim 7, wherein the distal portion is defined by an asymmetric V-shape.

11. A method for inserting an ocular implant into Schlemm's canal of an eye, comprising:
advancing a cannula through an anterior chamber of the eye, wherein the cannula comprises a curved tube, a trough portion disposed distally of the curved tube, and a distal portion disposed distally of the trough portion, wherein the distal portion is asymmetric with respect to a medial plane of the curved tube, wherein the distal portion comprises a distal segment and a proximal segment positioned proximally of the distal segment, wherein the distal segment has a cross-sectional curvature that is less curved than the cross-sectional curvature of the proximal segment of the distal portion;
inserting the distal portion into Schlemm's canal such that at least part of the trough portion is in fluid communication with Schlemm's canal; and
advancing the ocular implant through a lumen of the curved tube and along the trough portion into Schlemm's canal.

12. The method of claim 11, further comprising allowing a lower camming surface of the distal portion to contact a scleral spur of the eye to guide the distal portion and at least part of the trough portion into Schlemm's canal.

13. The method of claim 12, further comprising allowing an upper camming surface of the distal portion to contact scleral tissue of the eye to guide the distal portion and at least part of the trough portion into Schlemm's canal.

14. The method of claim 13, wherein the distal portion is asymmetric with respect to the medial plane of the curved tube due to the upper camming surface being shorter than the lower camming surface.

* * * * *